(12) United States Patent
Leonard et al.

(10) Patent No.: US 8,021,318 B2
(45) Date of Patent: *Sep. 20, 2011

(54) METHODS OF BLOOD-BASED THERAPIES HAVING A MICROFLUIDIC MEMBRANELESS EXCHANGE DEVICE

(75) Inventors: Edward F. Leonard, Bronxville, NY (US); Alan C. West, Tenafly, NJ (US); Nina C. Shapley, New York, NY (US); Zhongliang Tang, San Diego, CA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/942,519

(22) Filed: Nov. 9, 2010

(65) Prior Publication Data

US 2011/0056884 A1 Mar. 10, 2011

Related U.S. Application Data

(63) Continuation of application No. 12/509,395, filed on Jul. 24, 2009, now Pat. No. 7,850,633, which is a continuation of application No. 11/127,905, filed on May 12, 2005, now abandoned, which is a continuation-in-part of application No. 10/801,366, filed on Mar. 15, 2004, now abandoned, and a continuation-in-part of application No. PCT/US2004/007966, filed on Mar. 15, 2004.

(60) Provisional application No. 60/454,579, filed on Mar. 14, 2003.

(51) Int. Cl.
*A61M 1/34* (2006.01)
*B01D 61/24* (2006.01)
*B01D 61/14* (2006.01)
*B01D 61/38* (2006.01)

(52) U.S. Cl. ....... 604/5.04; 210/643; 210/645; 210/646; 210/767; 210/805; 604/4.01; 604/5.01; 604/6.09; 604/6.11; 604/6.16

(58) Field of Classification Search .......... 210/200, 210/201, 252, 258, 321.6, 456, 645, 646, 210/642, 643, 767, 805, 806; 422/100, 101, 422/104; 604/4.01, 5.01, 5.04, 6.09, 6.11, 604/6.16
See application file for complete search history.

(56) References Cited

U.S. PATENT DOCUMENTS 2,885,782 A 5/1959 Groves
(Continued)

FOREIGN PATENT DOCUMENTS

DE 20113789 5/2002
(Continued)

OTHER PUBLICATIONS

Abbitt et al., "Rheological Properties of the Blood Influencing Selectin-Mediated Adhesion of Flowing Leukocytes." American Journal of Physiology: Heart and Circulatory Physiology, Jul. 2003, 285(1): pp. H229-H240.

(Continued)

*Primary Examiner* — John Kim
(74) *Attorney, Agent, or Firm* — Miles & Stockbridge P.C.; Mark A. Catan

(57) ABSTRACT

The present invention is directed to devices, systems and methods for removing undesirable materials from a sample fluid by contact with a second fluid. The sample fluid flows as a thin layer adjacent to, or between, concurrently flowing layers of the second fluid, without an intervening membrane. In various embodiments, a secondary separator is used to restrict the removal of desirable substances and effect the removal of undesirable substances from blood. The invention is useful in a variety of situations where a sample fluid is to be purified via a diffusion mechanism against an extractor fluid. Moreover, the invention may be used for the removal of components from a sample fluid that vary in size. When blood is the sample fluid, for example, this may include the removal of 'small' molecules, 'middle' molecules, macromolecules, macromolecular aggregates, and cells, from the blood sample to the extractor fluid.

18 Claims, 14 Drawing Sheets

U.S. PATENT DOCUMENTS

| | | |
|---|---|---|
| 3,388,803 A | 6/1968 | Scott |
| 3,506,126 A | 4/1970 | Lindsay et al. |
| 3,619,423 A | 11/1971 | Galletti et al. |
| 3,746,175 A | 7/1973 | Markley |
| 3,799,873 A | 3/1974 | Brown |
| 3,884,808 A | 5/1975 | Scott |
| 3,939,069 A | 2/1976 | Granger et al. |
| 3,989,622 A | 11/1976 | Marantz et al. |
| 3,994,799 A | 11/1976 | Yao et al. |
| 4,066,549 A | 1/1978 | Oeser et al. |
| 4,083,786 A | 4/1978 | Tsuda et al. |
| 4,094,775 A | 6/1978 | Mueller |
| 4,137,921 A | 2/1979 | Okuzumi et al. |
| 4,153,554 A | 5/1979 | von der Heide et al. |
| 4,166,800 A | 9/1979 | Fong |
| 4,181,983 A | 1/1980 | Kulkarni |
| 4,212,738 A | 7/1980 | Henne |
| 4,212,742 A | 7/1980 | Solomon et al. |
| 4,243,775 A | 1/1981 | Rosensaft et al. |
| 4,247,393 A | 1/1981 | Wallace |
| 4,267,040 A | 5/1981 | Schal |
| 4,269,708 A | 5/1981 | Bonomini et al. |
| 4,279,249 A | 7/1981 | Vert et al. |
| 4,300,565 A | 11/1981 | Rosensaft et al. |
| 4,321,192 A | 3/1982 | Jain |
| 4,347,234 A | 8/1982 | Wahlig et al. |
| 4,384,975 A | 5/1983 | Fong |
| 4,390,519 A | 6/1983 | Sawyer |
| 4,394,370 A | 7/1983 | Jefferies |
| 4,409,332 A | 10/1983 | Jefferies et al. |
| 4,431,019 A | 2/1984 | Kopp et al. |
| 4,443,333 A | 4/1984 | Mahurkar |
| 4,530,449 A | 7/1985 | Nozawa et al. |
| 4,538,603 A | 9/1985 | Pawelchak et al. |
| 4,539,981 A | 9/1985 | Tunc |
| 4,563,489 A | 1/1986 | Urist |
| 4,568,559 A | 2/1986 | Nuwayser et al. |
| 4,578,384 A | 3/1986 | Hollinger |
| 4,585,797 A | 4/1986 | Cioca |
| 4,596,574 A | 6/1986 | Urist |
| 4,623,588 A | 11/1986 | Nuwayser et al. |
| 4,661,246 A | 4/1987 | Ash |
| 4,663,049 A | 5/1987 | Kolff et al. |
| 4,678,566 A | 7/1987 | Watanabe et al. |
| 4,703,108 A | 10/1987 | Silver et al. |
| 4,741,337 A | 5/1988 | Smith et al. |
| 4,744,365 A | 5/1988 | Kaplan et al. |
| 4,765,899 A | 8/1988 | Wells et al. |
| 4,765,907 A | 8/1988 | Scott |
| 4,795,804 A | 1/1989 | Urist |
| 4,818,542 A | 4/1989 | DeLuca et al. |
| 4,822,278 A | 4/1989 | Oliva et al. |
| 4,837,285 A | 6/1989 | Berg et al. |
| 4,839,130 A | 6/1989 | Kaplan et al. |
| 4,844,854 A | 7/1989 | Kaplan et al. |
| 4,849,340 A | 7/1989 | Oberhardt |
| 4,877,864 A | 10/1989 | Wang et al. |
| 4,889,119 A | 12/1989 | Jamiolkowski et al. |
| 4,897,189 A | 1/1990 | Greenwood et al. |
| 4,898,186 A | 2/1990 | Ikada et al. |
| 4,898,734 A | 2/1990 | Mathiowitz et al. |
| 4,916,193 A | 4/1990 | Tang et al. |
| 4,938,763 A | 7/1990 | Dunn et al. |
| 4,961,707 A | 10/1990 | Magnusson et al. |
| 4,968,422 A | 11/1990 | Runge et al. |
| 4,968,590 A | 11/1990 | Kuberasampath et al. |
| 4,975,527 A | 12/1990 | Koezuka et al. |
| 4,997,570 A | 3/1991 | Polaschegg |
| 5,004,602 A | 4/1991 | Hutchinson |
| 5,007,939 A | 4/1991 | Delcommune et al. |
| 5,011,691 A | 4/1991 | Oppermann et al. |
| 5,011,692 A | 4/1991 | Fujioka et al. |
| 5,013,649 A | 5/1991 | Wang et al. |
| 5,037,639 A | 8/1991 | Tung |
| 5,051,272 A | 9/1991 | Hermes et al. |
| 5,077,049 A | 12/1991 | Dunn et al. |
| 5,080,665 A | 1/1992 | Jarrett et al. |
| 5,081,106 A | 1/1992 | Bentley et al. |
| 5,084,051 A | 1/1992 | Tormala et al. |
| 5,106,748 A | 4/1992 | Wozney et al. |
| 5,108,753 A | 4/1992 | Kuberasampath et al. |
| 5,108,755 A | 4/1992 | Daniels et al. |
| 5,114,932 A | 5/1992 | Runge |
| 5,116,738 A | 5/1992 | Wang et al. |
| 5,128,136 A | 7/1992 | Bentley et al. |
| 5,133,755 A | 7/1992 | Brekke |
| 5,141,905 A | 8/1992 | Rosen et al. |
| 5,143,730 A | 9/1992 | Fues et al. |
| 5,149,691 A | 9/1992 | Rutherford |
| 5,162,430 A | 11/1992 | Rhee et al. |
| 5,166,058 A | 11/1992 | Wang et al. |
| 5,171,217 A | 12/1992 | March et al. |
| 5,185,152 A | 2/1993 | Peyman |
| 5,187,076 A | 2/1993 | Wozney et al. |
| 5,192,741 A | 3/1993 | Orsolini et al. |
| 5,193,688 A | 3/1993 | Giddings |
| 5,197,977 A | 3/1993 | Hoffman, Jr. et al. |
| 5,206,028 A | 4/1993 | Li |
| 5,227,157 A | 7/1993 | McGinity et al. |
| 5,231,169 A | 7/1993 | Constantz et al. |
| 5,250,584 A | 10/1993 | Ikada et al. |
| 5,268,167 A | 12/1993 | Tung |
| 5,268,178 A | 12/1993 | Calhoun et al. |
| 5,271,961 A | 12/1993 | Mathiowitz et al. |
| 5,278,201 A | 1/1994 | Dunn et al. |
| 5,278,202 A | 1/1994 | Dunn et al. |
| 5,281,419 A | 1/1994 | Tuan et al. |
| 5,284,470 A | 2/1994 | Beltz |
| 5,284,559 A | 2/1994 | Lim et al. |
| 5,288,496 A | 2/1994 | Lewis |
| 5,308,623 A | 5/1994 | Fues et al. |
| 5,320,624 A | 6/1994 | Kaplan et al. |
| 5,324,307 A | 6/1994 | Jarrett et al. |
| 5,324,520 A | 6/1994 | Dunn et al. |
| 5,350,580 A | 9/1994 | Muchow et al. |
| 5,360,610 A | 11/1994 | Tice et al. |
| 5,366,508 A | 11/1994 | Brekke |
| 5,366,733 A | 11/1994 | Brizzolara et al. |
| 5,366,734 A | 11/1994 | Hutchinson |
| 5,376,636 A | 12/1994 | Rutherford et al. |
| 5,415,532 A | 5/1995 | Lougnane et al. |
| 5,437,857 A | 8/1995 | Tung |
| 5,460,803 A | 10/1995 | Tung |
| 5,534,244 A | 7/1996 | Tung |
| 5,562,895 A | 10/1996 | Tung |
| 5,577,891 A | 11/1996 | Lougnane et al. |
| 5,656,153 A | 8/1997 | Kameno et al. |
| 5,716,852 A | 2/1998 | Yager et al. |
| 5,725,776 A | 3/1998 | Kenley et al. |
| 5,744,042 A | 4/1998 | Stange et al. |
| 5,798,042 A | 8/1998 | Chu et al. |
| 5,833,954 A | 11/1998 | Chow et al. |
| 5,855,562 A | 1/1999 | Moore et al. |
| 5,871,360 A | 2/1999 | Kato |
| 5,885,829 A | 3/1999 | Mooney et al. |
| 5,902,336 A | 5/1999 | Mishkin |
| 5,917,322 A | 6/1999 | Gershenfeld et al. |
| 5,932,100 A | 8/1999 | Yager et al. |
| 5,944,684 A | 8/1999 | Roberts et al. |
| 5,948,684 A | 9/1999 | Weigl et al. |
| 5,980,481 A | 11/1999 | Gorsuch |
| 5,984,891 A | 11/1999 | Keilman et al. |
| 5,993,786 A | 11/1999 | Chow et al. |
| 6,000,341 A | 12/1999 | Tung |
| 6,001,897 A | 12/1999 | Dickens |
| 6,056,930 A | 5/2000 | Tung |
| 6,114,408 A | 9/2000 | Dickens |
| 6,117,100 A | 9/2000 | Powers et al. |
| 6,117,122 A | 9/2000 | Din et al. |
| 6,128,764 A | 10/2000 | Gottesman |
| 6,159,739 A | 12/2000 | Weigl et al. |
| 6,187,838 B1 | 2/2001 | Dickens |
| 6,196,992 B1 | 3/2001 | Keilman et al. |
| 6,197,494 B1 | 3/2001 | Oberhardt |
| 6,206,959 B1 | 3/2001 | Dickens |
| 6,210,759 B1 | 4/2001 | Dickens |
| 6,281,256 B1 | 8/2001 | Harris et al. |

| | | |
|---|---|---|
| 6,317,766 B1 | 11/2001 | Grover |
| 6,332,985 B1 | 12/2001 | Sherman et al. |
| 6,398,859 B1 | 6/2002 | Dickens et al. |
| 6,406,631 B1 | 6/2002 | Collins et al. |
| 6,413,498 B1 | 7/2002 | Malmagro |
| 6,432,630 B1 | 8/2002 | Blankenstein |
| 6,459,097 B1 | 10/2002 | Zagoskin |
| 6,472,210 B1 | 10/2002 | Holy et al. |
| 6,488,896 B2 | 12/2002 | Weigl et al. |
| 6,504,172 B2 | 1/2003 | Zagoskin et al. |
| 6,511,814 B1 | 1/2003 | Carpenter |
| 6,527,735 B1 | 3/2003 | Davankov et al. |
| 6,551,842 B1 | 4/2003 | Carpenter |
| 6,561,997 B1 | 5/2003 | Weitzel et al. |
| 6,563,311 B2 | 5/2003 | Zagoskin |
| 6,582,385 B2 | 6/2003 | Burbank et al. |
| 6,585,682 B1 | 7/2003 | Haraldsson et al. |
| 6,602,719 B1 | 8/2003 | Carpenter |
| 6,605,822 B1 | 8/2003 | Blais et al. |
| 6,614,047 B2 | 9/2003 | Tzalenchuk et al. |
| 6,670,630 B2 | 12/2003 | Blais et al. |
| 6,742,661 B1 | 6/2004 | Schulte et al. |
| 6,743,626 B2 | 6/2004 | Baum et al. |
| 6,758,975 B2 | 7/2004 | Peabody et al. |
| 6,784,451 B2 | 8/2004 | Amin et al. |
| 6,793,725 B2 | 9/2004 | Chow et al. |
| 6,796,955 B2 | 9/2004 | O'Mahoney et al. |
| 6,803,599 B2 | 10/2004 | Amin et al. |
| 6,897,468 B2 | 5/2005 | Blais et al. |
| 6,899,915 B2 | 5/2005 | Yelick et al. |
| 6,900,456 B2 | 5/2005 | Blais et al. |
| 6,911,664 B2 | 6/2005 | Il'ichev et al. |
| 6,930,320 B2 | 8/2005 | Blais et al. |
| 7,002,174 B2 | 2/2006 | Il'ichev et al. |
| 7,052,907 B2 | 5/2006 | Shi et al. |
| 7,118,676 B2 | 10/2006 | Mueth et al. |
| 7,150,834 B2 | 12/2006 | Mueth et al. |
| 7,309,232 B2 | 12/2007 | Rutherford et al. |
| 7,309,323 B2 | 12/2007 | Gura et al. |
| 7,351,218 B2 | 4/2008 | Bene |
| 7,588,550 B2 | 9/2009 | Leonard et al. |
| 2001/0048637 A1 | 12/2001 | Weigl et al. |
| 2001/0055546 A1 | 12/2001 | Weigl et al. |
| 2002/0052571 A1 | 5/2002 | Fazio |
| 2002/0090644 A1 | 7/2002 | Weigl et al. |
| 2002/0159920 A1 | 10/2002 | Weigl |
| 2002/0172622 A1 | 11/2002 | Weigl et al. |
| 2002/0188578 A1 | 12/2002 | Amin et al. |
| 2003/0034306 A1 | 2/2003 | Schulte et al. |
| 2003/0193097 A1 | 10/2003 | Il'ichev et al. |
| 2003/0224944 A1 | 12/2003 | Il'ichev et al. |
| 2003/0226806 A1 | 12/2003 | Young et al. |
| 2004/0009096 A1 | 1/2004 | Wellman |
| 2004/0012407 A1 | 1/2004 | Amin et al. |
| 2004/0016918 A1 | 1/2004 | Amin et al. |
| 2004/0045891 A1 | 3/2004 | Gilbert et al. |
| 2004/0069708 A1 | 4/2004 | Laurell et al. |
| 2004/0082903 A1 | 4/2004 | Micheli |
| 2004/0225249 A1 | 11/2004 | Leonard et al. |
| 2004/0245102 A1 | 12/2004 | Gilbert et al. |
| 2005/0082210 A1 | 4/2005 | Favre |
| 2005/0101901 A1 | 5/2005 | Gura |
| 2005/0121604 A1 | 6/2005 | Mueth et al. |
| 2005/0178727 A1 | 8/2005 | Takagi et al. |
| 2005/0201903 A1 | 9/2005 | Weigl et al. |
| 2005/0202563 A1 | 9/2005 | Dasgupta et al. |
| 2005/0215936 A1 | 9/2005 | Gorsuch et al. |
| 2006/0076295 A1 | 4/2006 | Leonard et al. |
| 2007/0029257 A1 | 2/2007 | Mueth et al. |
| 2007/0179436 A1 | 8/2007 | Braig et al. |
| 2008/0009780 A1 | 1/2008 | Leonard et al. |
| 2008/0015487 A1 | 1/2008 | Szamosfalvi et al. |
| 2008/0093298 A1 | 4/2008 | Browning et al. |
| 2009/0139931 A1 | 6/2009 | Leonard et al. |
| 2010/0004578 A1 | 1/2010 | Leonard et al. |

FOREIGN PATENT DOCUMENTS

| | | |
|---|---|---|
| EP | 1622691 | 2/2006 |
| EP | 2019658 | 2/2009 |
| JP | 10-507962 | 8/1998 |
| JP | 2000-512541 | 9/2000 |
| JP | 2001-511520 | 8/2001 |
| JP | 2002-509248 | 3/2002 |
| JP | 2006-520246 | 9/2006 |
| JP | 11-508182 | 7/2009 |
| WO | WO 02/036246 | 5/2002 |
| WO | WO 02/045813 | 6/2002 |
| WO | WO 02/062454 | 8/2002 |
| WO | WO 2004/082796 | 9/2004 |
| WO | WO 2006/124431 | 11/2006 |
| WO | WO 2007/137245 | 11/2007 |
| WO | WO 2009/100154 | 8/2009 |

OTHER PUBLICATIONS

Blackshear, P.L., "Two new concepts that might lead to a wearable artificial kidney," Kidney International, Supplement, Jun. 1978, 8:S133-S137.

Giddings, J.C., "Continuous Separation In Split-Flow Thin (Splitt) Cells Potential Applications To Biological Materials." Separation Science And Technology, 1988, 23(8& 9) : pp. 931-943.

Goldsmith et al., "Margination of Leukocytes in Blood Flow Through Small Tubes" Microvascular Research, Mar. 1984, 27(2): pp. 204-222.

Harper, G., "Home Hemodialysis: A Patient's Perspective." Home Hemodialysis International, 1997, 1: pp. 8-11.

Henne et al, "A Wearable Artificial-Kidney," Artificial Organs, 1977, 1(1): p. 126.

Leonard et al., "Dialysis without Membranes: How and Why?," Blood Purification, 2004, 22 (1):pp. 92-100.

Leonard et al., "Membraneless Dialysis—Is it Possible?" Contributions to Nephrology, 2005, 149: pp. 343-353.

Levin et al., "Analytical Splitt Fractionation In The Diffusion Mode Operating as a Dialysis-Like System Devoid of Membrane—Application To Drug-Carrying Liposomes." Analytical Chemistry, 1993, 65(17): pp. 2254-2261.

Neff et al., "A Wearable Artificial Glomerulus," Transactions—American Society for Artificial Internal Organs, 1979, 25: pp. 71-73.

Ronco, C., "Microfluidic, Membrane-Free Dialysis," American Society of Nephrology, Annual Meeting. 2002.

Schmuhl et al., "Si-Supported Mesoporous and Microporous Oxide Interconnects as Electrophoretic Gates for Application in Microfuidic Devices." Analytical Chemistry, Jan. 2005, 77(1): pp. 178-184.

Seo et al., "Improvement Of The Wearable Artificial Kidney," International Journal of Artificial Organs, 1981, 5(3): pp. 321.

Singh et al., "Haematocrit Dependence Of Cellular Axial Migration And Tubular Pinch Effects In Blood Flow Through Glass Capillaries," Current Science, Feb. 1990, 59(4): pp. 223-226.

Takai et al., "A New Treatment Strategy Using Both Intermittent Short Dialysis and Continuous Ambulatory Hemofiltration," Transactions of the American Society for Artificial Internal Organs, 1991, 37(3):pp. M325-M327.

Takayama et al., "Topographical Micropatterning of Poly(dimethylsiloxane) Using Laminar Flows of Liquids in Capillaries," Advanced Materials, Apr. 2001, 13(8): pp. 570-574.

Vanholder et al., "Pitfalls of Wearable Artificial-Kidney," International Journal Of Artificial Organs, 1990, 13(11): pp. 715-719.

METHODS OF BLOOD-BASED THERAPIES HAVING A MICROFLUIDIC MEMBRANELESS EXCHANGE DEVICE

CROSS-REFERENCE TO RELATED APPLICATION

This application is a continuation of U.S. application Ser. No. 12/509,395, filed Jul. 24, 2009, now U.S. Pat. No. 7,850,633, which is a continuation of U.S. application Ser. No. 11/127,905, filed May. 12, 2005, abandoned, which is a continuation-in-part of and claims the benefit of U.S. application Ser. No. 10/801,366, filed Mar. 15, 2004, abandoned, and is a continuation-in-part of PCT International Application No. PCT/US04/07966, filed Mar. 15, 2004, both of which claim the benefit of U.S. Provisional Patent Application No. 60/454,579, filed Mar. 14, 2003, expired, each of which is hereby incorporated by reference herein in its entirety.

FIELD OF THE INVENTION

Generally speaking, the present invention relates to the purification of a sample fluid. More particularly, the present invention relates to the purification of a sample fluid (e.g., blood fluid) by selectively removing components using a microfluidic membraneless exchange device.

BACKGROUND OF THE INVENTION

Extracorporeal processing of blood is known to have many uses. Such processing may be used, for example, to provide treatment of a disease. Hemodialysis is the most commonly employed form of extracorporeal processing for this purpose. Additional uses for extracorporeal processing include extracting blood components useful in either treating others or in research. Apheresis of plasma (i.e., plasmapheresis) and thrombocytes, or platelets, are the procedures most commonly employed for this purpose.

Many different extracorporeal blood processing processes have been developed, each of which seeks to remove certain components from the blood, depending on the reason for processing the blood. (It will be understood that as used herein, blood, or blood fluid, refers to any fluid having blood components from which extraction of certain components, such as toxins or metabolites present in excess, is desired.) The most common process utilizes an artificial membrane of substantial area, across which selected blood components are induced to flow. This flow is generally induced by a trans-membrane difference in either concentration or pressure, or a combination of the two. Another form of blood processing calls for the separation of certain components from blood by passing the blood over sorbent particles. In yet other forms of blood processing, not practiced as commonly, blood is directly contacted with an immiscible liquid (e.g., a fluorocarbon liquid), with the desired result being the removal of dissolved carbon dioxide and the provision of oxygen. The usefulness of blood processing techniques employing immiscible liquids is limited, however, because these immiscible liquids generally have very limited capacity to accept the blood components that it is desirable to extract.

One common example of a therapeutic use for blood processing is the mitigation of the species and volume imbalances accompanying end-stage renal disease. The population of patients treated in this manner (i.e., through hemodialysis) exceeds 260,000 and continues to grow, with the cost of basic therapy exceeding $5 billion per year excluding complications. The overwhelming majority of these patients (about 90%), moreover, are treated in dialysis centers, generally in thrice-weekly sessions. While procedures have been—and continue to be—refined, the components and the geometry of hemodialysis were largely fixed in the 1970's: a bundle of several thousand, permeable hollow fibers, each about 25 cm long and about 200 μm internal diameter, perfused externally by dialyzing solution, with the device operated principally in a diffusive mode but with a transmembrane pressure applied to induce a convective outflow of water. Upward of 120 liters per week of patient blood are dialyzed against upwards of 200 liters per week of dialyzing solution, often in three weekly treatments that total as little as seven to nine hours per week. These numbers vary somewhat, and competing technologies exist, but the basic approach just described predominates.

Despite the benefits of therapies (e.g., hemodialysis) using the various forms of blood processing described above, the prolongation of life achieved is complicated by the progression and complexity of the disease the therapies are used to treat (few patients on dialysis are ever completely rehabilitated), and by several problems that are innate to the therapies themselves. For example, problems arise with blood processing as a result of the contact of blood with extensive areas of artificial membrane (as in the case of hemodialysis), and well as the contact of blood with sorbents or immiscible fluids as described above. In particular, this contact often induces biochemical reactions in the blood being processed, including the reactions that are responsible for clotting, activation of the complement system, and irreversible aggregation of blood proteins and cells.

Another problem associated with known blood processing techniques is that the contact of blood with an artificial membrane (or another medium, such as a surface of a sorbent or immiscible fluid) is likely to cause the blood-medium interface to become fouled. It is generally known that therapeutic interventions (e.g., those related to end-stage renal disease) are optimally conducted with slow delivery and in as nearly a continuous fashion as possible, in emulation of the continuous action of a natural kidney. However, fouling caused by the contact of blood with the medium limits the time that a device which contains these interfaces can be usefully employed. As a result, portable blood processing devices become impractical, and patients are generally forced to undergo the type of episodic dialysis schedule described above, which creates many negative side effects such as physical exhaustion and excessive thirst. Moreover, even while daily dialysis (e.g., 1.5-2.0 hours, six days per week) or nocturnal dialysis (e.g., 8-10 hours, 6-7 nights per week) improves this situation by extending treatment times, a patient using one of these forms of treatment or a partner is required to master technical procedures and, as many find especially onerous, to access patient blood by the insertion of usually two relatively large needles into a vein or artificial, subcutaneous fistula.

In light of the above, it would be desirable to provide techniques for processing blood in which treatment times are extended (with consequently lower rates of flow) and that do not require a patient to initiate and terminate blood access. Moreover, it would also be desirable to provide techniques for processing blood that eliminate (or at least reduce) the inducement of undesirable biochemical reactions, and where the blood-medium interfaces do not become fouled.

SUMMARY OF THE INVENTION

The above and other deficiencies associated with existing blood processing processes are overcome in accordance with the principles of the present invention which are described below. According to one aspect of the invention, a membraneless exchange device for extracting components from a sample fluid is described which includes first, second and third inlet channels, first, second and third exit channels and a microfluidic extraction channel connected to the first, second and third inlet channels and the first, second and third exit channels and a flush port. Moreover, laminar flows of a first extractor fluid, the sample fluid, and a second extractor fluid are established inside the extraction channel, and sheathing of the sample fluid by the first and second extractor fluids substantially limits contact between the sample fluid and the surfaces of the extraction channel.

According to another embodiment of the present invention, a system for performing hemodialysis is provided which includes a membraneless exchange device including first and second dialysate inlet channels, blood inlet and exit channels, first and second dialysate exit channels and a microfluidic dialysis channel connected to the first and second dialysate inlet and outlet channels and the blood inlet and exit channels. Moreover, laminar flows of a first dialysate fluid, blood fluid, and a second dialysate fluid are established in order inside the dialysis channel, and at least some of the components of the blood fluid exit the device through the first and second dialysate exit channels. Additionally, according to the invention, a secondary processor receives the dialysate fluid and the at least some of the components of the blood fluid exiting the device through the first and second dialysate exit channels.

In yet another embodiment of the present invention, a method for extracting components from a sample fluid is provided which includes establishing laminar flows of a first extractor fluid, the sample fluid and a second extractor fluid inside a microfluidic extraction channel. Sheathing of the sample fluid by the first and second extractor fluids, moreover, substantially limits contact between the sample fluid and the surfaces of the extraction channel. The method further includes withdrawing the first extractor fluid, the sample fluid and the second extractor fluid from the extraction channel such that at least a portion of the sample fluid is removed together with the first extractor fluid and the second extractor fluid and apart from the remainder of the sample fluid.

A method for performing hemodialysis is also provided which includes establishing laminar flows of a first dialysate fluid, blood fluid and a second dialysate fluid inside a microfluidic extraction channel, withdrawing the first dialysate fluid, the blood fluid and the second dialysate fluid from the extraction channel such that at least some of the components of the blood fluid are removed together with the first dialysate fluid and the second dialysate fluid and apart from the remainder of the blood fluid, and providing the first and second dialysate fluids and the at least some of the components of the blood fluid to a secondary processor.

In general, however, the present invention is directed toward microfluidic membraneless exchange devices and systems, and methods of making the same, for selectively removing undesirable materials from a sample fluid (e.g., blood fluid) by contact with a miscible fluid (extractor fluid or secondary fluid, e.g., dialysate). A microfluidic device, as considered in this application, has channels whose height is less than about 0.6 mm, where "height" is the dimension perpendicular to the direction of flow and also perpendicular to the interfacial area across which transport occurs. For example, flow patterns and species exchanges occur when blood is flowed as a thin layer adjacent to, or between, concurrently flowing layers of a secondary fluid, without an intervening membrane. The secondary fluid, moreover, is generally miscible with blood and diffusive and convective transport of all components is expected. The following reference which refers to membraneless devices described below is hereby incorporated by reference in its entirety: Leonard et al., Dialysis without Membranes: How and Why?, Blood Purification 22 (1) 2004 92-100.

Sheathing a core of blood with the miscible fluid, or assuring that the miscible fluid lies between at least a substantial portion of the blood and the enclosing boundaries of the flow path, prevents or at least limits contact of the blood with these boundaries. In turn, this configuration of the two fluids prevents or at least reduces the undesirable activation of factors in the blood, thereby minimizing bioincompatibilities that have been problematic in prior techniques of blood processing.

The invention also eliminates or at least substantially reduces the fouling reactions that have been known to be a major deterrent to the continuous use of an extracorporeal extraction device. In particular, as the primary transport surface in the membraneless exchange device (also referred to herein as a membraneless separator) of the invention is intrinsically non-fouling, a major deterrent to long-term or continuous operation is removed, opening the possibility to the design and construction of small, wearable devices or systems with the recognized benefits of nearly continuous blood treatment. Such a device or system could be very small and worn or carried by the patient (e.g., outside of a hospital or clinic setting), and could be supplied with external buffer reservoirs (in a back-pack, briefcase, or from a reservoir located in the home, located at the place of work, etc.). Further, because fouling would be reduced, and sustained operation at low blood flows over long times would be allowed, such anticoagulation as might be required is likely to have an effect confined to the extracorporeal circuit. As understood by those skilled in the art, avoiding systemic anticoagulation outside of the clinic is highly desirable.

The devices, systems and methods of the invention described herein also have the benefit of being capable of diffusing various blood components having different sizes. In particular, the flow of blood and a miscible fluid with which it is in contact can be controlled for the purpose of achieving the desired separation of components. For example, flow adjustment can minimize cellular migration across the interface. A sheath fluid can be used to give the discrimination of a membrane between large and small molecules that cannot be achieved by a denuded interface, no matter how exposure time (adjacent flows) is varied. For example, as explained below, various flow conditions may be used that cause blood cells to move away from the blood-liquid interface, thereby making it is possible to "skim" blood in order to remove substantial amounts of plasma, without cells.

As also discussed below, membraneless contact of a thin layer of blood with a sheathing fluid according to the present invention may be used to cause high rates of exchange per unit area of blood-sheathing fluid contact for all solutes, but with a discrimination among free (unbound) solutes that is less than the square-root of the ratio of their diffusion coefficients. Moreover, while high exchange rates (e.g., of toxic substances) are often desirable, indiscriminate transport is not. Therefore, according to the principles of the present invention, a membraneless exchange device as described herein is used in conjunction with at least one secondary processor (e.g., a membrane device or other type of separator) in order to restrict the removal of desirable substances and effect the removal of undesirable substances from blood. The efficiency of such a secondary separator is greatly increased by the use of a primary separator that is capable of delivering cell-depleted (or cell-free) fractions of blood to it. Therefore, according to another aspect of this invention, transport of molecular components of blood to the sheathing fluid may be indiscriminate. The sheathing fluid, carrying both molecular components which are, and those which are not, desirable to remove from blood, is provided to the secondary separator, such that the fluid entering the secondary separator is substantially cell-free. The secondary separator, meanwhile, regulates the operation of the membraneless separator through the composition of the recycle stream that it returns (directly or indirectly) to the sheath fluid inlets of the membraneless separator. According to the principles of the present invention, moreover, a membrane-based secondary separator used in this manner is able to achieve much higher separation rates because concentration polarization (i.e., the accumulation of material rejected by the secondary separator on the upstream side of the separator) is limited to proteins and does not involve cells. Moreover, because cells would be retained in the primary separator (i.e., the membraneless exchange device), they would see artificial material only on its conduit surfaces, not on its liquid-liquid contact area, whence bioincompatibilities should be much reduced. As such, it should be understood that the need for anticoagulation may be greatly reduced or eliminated.

There is a need to establish and break extracorporeal blood flow. In plain terms, patients dislike the needle sticks and even the needle withdrawals associated with home dialysis and which are necessitated by any dialysis system whose sterile parts are not small enough to travel with or within the patient. While the present invention still requires a connect/disconnect, it is done at the washing fluid interface. The extracorporeal blood flow is continuous and because blood sees no membrane it can function indefinitely without need to interrupt the blood flow. Further features of the invention, its nature and various advantages, will be more apparent upon consideration of the following detailed description, taken in conjunction with the accompanying drawings, in which like reference characters refer to like parts throughout.

DETAILED DESCRIPTION OF THE INVENTION

Figure 12:
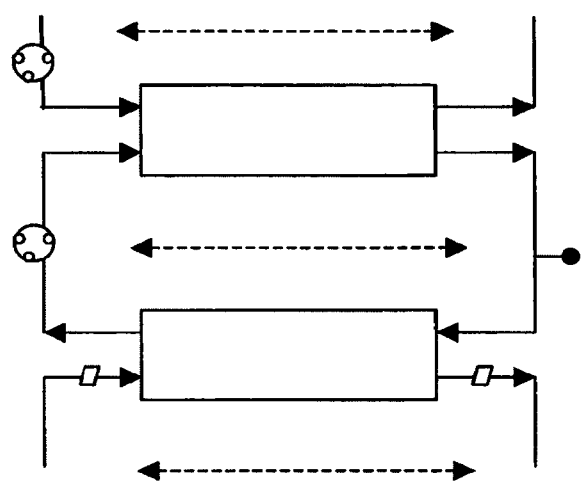
FIG. 12 is a diagram showing how blood and sheath fluid circulate together through the blood-sheath contractor, driven by a 2-headed peristaltic pump. The flush port is shown. Blood returns to patient. Sheath fluid enters membrane dialyzer and is then recirculated to the blood-sheath contactor. Dialysate, when connected, flows countercurrent to sheath fluid in a membrane dialyzer. Blood and sheath fluid flow at all times. Dialysis is effective when dialysate is connected. With a device to maintain trans-membrane pressure in the dialyzer, ultrafiltration can occur in the absence of dialysate. The flush port allows for periodic injection of sterile saline into the sheath stream in order to force cells back into bloodstream. Of course, it is likely not possible to keep all cells out of the sheath fluid. The removal of cells that find their way into the sheath fluid is more complicated, and less desirable than returning the cells to the bloodstream. In the case where the cells accumulate to concentrations in the sheath fluid that are undesirable, a periodic flush can be utilitzed. The volume of the flush need only be a small fraction of all fluid removed by the secondary separator. The flush allows for effective return of these cells to the bloodstream, and clarification of the sheath fluid.

According to one aspect of the invention, a membraneless exchange device for extracting components from a sample fluid is described which includes first, second and third inlet channels, first, second and third exit channels and a microfluidic extraction channel connected to the first, second and third inlet channels and the first, second and third exit channels, and which includes a flush port. One embodiment of the flush port is depicted in FIG. 12. The flush port is capable of 'reverse flushing'. In usage of the device of the invention, there may be cells entering the sheath fluid and this is undesirable. If no correction is applied (some method of removing the cells from the sheath fluid, or some method of returning the cells to the blood), it is inevitable that the composition of the sheath fluid, over a long enough period of time, will approach that of blood, thus obviating many if not all of the advantages of the invention. While there are many ways of refreshing the sheath fluid (such as filtration or simply discarding and replacing it) it is preferable that the cells that had entered the sheath fluid be periodically returned to the blood. If there has been active removal in the sheath circuit of toxins and superfluous metabolites, the quantity of these materials returned to the patient along with the cells will be negligible and valuable cells will not be lost. It will be appreciated that cells entering the sheath fluid have only these possible fates: (1) to be destroyed, which is generally undesirable unless the products of the destruction are removed, since these products may be harmful if returned to the patient, (2) to be removed from the system by accumulation on a filter, which presents numerous technical difficulties, or (3) to be returned to the blood stream. The latter fate is the most desirable. If it is, however, achieved only when the sheath fluid reaches the same cell concentration as blood, much of the benefit of providing the sheath will be lost. Thus, the benefits of sheathing are preserved by periodically forcing the return of cells by the simple flushing process described. So long as the volume of sheath fluid and the substances contained in it are small compared with the volume of fluid removed since the last flush, any interruption of the removal process is inconsequential. For example, one embodiment of the invention provides water extraction from blood at a rate of 3 ml/min. In this embodiment, the total volume of sheath fluid is approximately 3-5 ml. If this fluid is displaced by fresh, sterile saline, it will be necessary to remove that much additional fluid from the system, but that can be accomplished in less than 2 minutes. In one embodiment of the invention, flushing will be carried out about not more than once an hour. In other embodiments, the flushing will be carried out about twice an hour, about once every two hours, about once every 2.5 hours, about once every 3 hours, about once every 3.5 hours, about once every 4 hours, about once every 4.5 hours, about once every 5 hours, or less often. Thus, in this embodiment, the time of treatment necessary to achieve a given amount of removal of toxins and surplus metabolites, including water, will be increased by not more than 3%.

The membraneless device of the invention utilizes laminar flows within the device. Laminar flows of a first extractor fluid, the sample fluid, and a second extractor fluid are established inside the extraction channel, and sheathing of the sample fluid by the first and second extractor fluids substantially limits contact between the sample fluid and the surfaces of the extraction channel. In one embodiment of the device, at least 90% of the sample fluid is sheathed by the first and second extractor fluids. In other embodiments, 95% of the sample fluid is sheathed. In yet other embodiments, at least a portion of the sample fluid exits the device with the first extractor fluid through the first exit channel, and advective transport of molecules within said extraction channel is substantially nonexistent. The composition of the first extractor fluid, moreover, is substantially the same as the composition of the second extractor fluid is various embodiments. In other preferred embodiments, the sample fluid flow is between the first and second extractor fluid flows. Moreover, a first diverter is formed from a portion of the first exit channel and a portion of the second exit channel, while a second diverter is formed from a portion of the second exit channel and a portion of the third exit channel. It should also be understood that the device may include a first interface formed between the first extractor fluid flow and the sample fluid flow that is aligned with at least a portion of the first diverter, and may also include a second interface formed between the second extractor fluid flow and the sample fluid flow that is aligned with at least a portion of the second diverter. In various embodiments of the invention, moreover, the sample fluid is blood fluid, in which case it is contemplated that the components extracted from the sample fluid are non-cellular components of the blood fluid. Additionally, the device may use a first pump for controlling the flow of extractor fluid in the extraction channel, and may use a second pump for controlling the flow of sample fluid in the extraction channel. When a first pump is used, it may be an injection pump that controls the flow of extractor fluid into the extraction channel, and a withdrawal pump may be used that controls the flow of extractor fluid out of the extraction channel. In one embodiment, one pump controls three (3) streams (or five, if the two extractor fluids are considered to be separate). In such a case, the flow rate of the 6th stream is then determined by physics. In this case, the sixth stream is the existing blood from the patient. In this case, therefore, the fraction of the blood volume that is removed is controlled by accurately setting the other pumps. Anything else, absent a membrane, does not give the control that is needed. In one embodiment, the pump used should control differentially the flow extraction in and out of the device so that the forces are controlled and thus prescribes the volume of fluid taken from the blood stream.

In various embodiments, additionally, a source of extractor fluid is connected to said first inlet channel and a source of sample fluid connected to said second inlet channel. It will be understood that the source of sample fluid can be, for example, a human being. In preferred embodiments, moreover, the extraction channel of the device according to the invention has a height of less than 600 μm, and has a width-to-height ratio of at least ten. The device may also be used in a system for extracting components from a sample fluid, where the system also includes a secondary processor that receives the first extractor fluid, the second extractor fluid and at least some of the components of the sample fluid upon exiting the extraction channel. It will be understood that the secondary processor may be, for example, a membrane device or a sorption device or a reactor capable of transforming components of the sample fluid.

According to another embodiment of the present invention, a system for performing hemodialysis is provided which includes a membraneless exchange device including first and second dialysate inlet channels, blood inlet and exit channels, first and second dialysate exit channels and a microfluidic dialysis channel connected to the first and second dialysate inlet and outlet channels and the blood inlet and exit channels. Moreover, laminar flows of a first dialysate fluid, blood fluid, and a second dialysate fluid are established in order inside the dialysis channel, and at least some of the components of the blood fluid exit the device through the first and second dialysate exit channels. Additionally, according to the invention, a secondary processor receives the dialysate fluid and the at least some of the components of the blood fluid exiting the device through the first and second dialysate exit channels. In various embodiments, the secondary processor filters the dialysate fluid and the at least some of the components of the blood fluid exiting the device through the first and second dialysate exit channels, and returns the filtered fluid to the first and second dialysate inlet channels. In certain preferred embodiments, these components of the blood fluid are substantially non-cellular components of the blood fluid. In other embodiments, sheathing of the blood fluid by the first and second dialysate fluids substantially limits contact between the blood fluid and the surfaces of the dialysis channel. Moreover, the secondary processor may be a membrane device, or may be a sorption device, for example. It will also be understood that the composition of the first dialysis fluid may be substantially the same as the composition of the second dialysis fluid. According to other aspects of the invention, meanwhile, a first diverter is formed from a portion of the first dialysate exit channel and a portion of the blood exit channel, and a second diverter is formed from a portion of the blood exit channel and a portion of the second dialysate exit channel. A first pump for controlling the flow of dialysate fluid in the dialysis channel and a second pump for controlling the flow of blood fluid in the dialysis channel may also be used in accordance with the principles of the present invention. According to several embodiments, the interface between the first dialysate fluid and the blood fluid is varied by adjusting the volumetric flow rates of the first dialysate fluid and the blood fluid. In other embodiments, the interface between the blood fluid and the second dialysate fluid is varied by adjusting the volumetric flow rates of the blood fluid and the second dialysate fluid. Additionally, a detector for detecting a presence of an undesired blood component within the dialysate fluid upon exiting the dialysis chamber may be used. In this case, for example, the detector is a photo detector. According to another aspect of the invention, a first pump for controlling the flow of dialysate fluid in the dialysis channel is adjusted based on said detected presence of an undesired blood component within said dialysate fluid. Moreover, for example, the velocities of the laminar flows of the first dialysate fluid, the blood fluid and the second dialysate fluid are adjusted based on the detected presence of an undesired blood component within the first and second dialysate fluids according to the invention. Additionally, according to the invention, the first and second dialysate fluids may include at least one of the following: a hyper osmolar solution, a solution high in glucose content, or a polyelectrolye osmotic agent.

In yet another embodiment of the present invention, a method for extracting components from a sample fluid is provides which includes establishing laminar flows of a first extractor fluid, the sample fluid and a second extractor fluid inside a microfluidic extraction channel. Sheathing of the sample fluid by the first and second extractor fluids, moreover, substantially limits contact between the sample fluid and the surfaces of the extraction channel. The method further includes withdrawing the first extractor fluid, the sample fluid and the second extractor fluid from the extraction channel such that at least a portion of the sample fluid is removed together with the first extractor fluid and the second extractor fluid and apart from the remainder of the sample fluid. According to the invention, moreover, establishing laminar flows includes providing first, second and third inlet channels and providing first, second and third exit channels. Additionally, for example, the method includes providing the first and second extractor fluids and the at least a portion of the sample fluid to a secondary processor.

A method for performing hemodialysis is also provided which includes establishing laminar flows of a first dialysate fluid, blood fluid and a second dialysate fluid inside a microfluidic extraction channel, withdrawing the first dialysate fluid, the blood fluid and the second dialysate fluid from the extraction channel such that at least some of the components of the blood fluid are removed together with the first dialysate fluid and the second dialysate fluid and apart from the remainder of the blood fluid, and providing the first and second dialysate fluids and the at least some of the components of the blood fluid to a secondary processor. In various embodiments, the method also includes using the secondary processor to filter the first and second dialysate fluids and the at least some of the components of the blood fluid, as well as returning the filtered fluid from the secondary processor to the extraction channel. In yet other embodiments, the method includes sheathing the blood fluid by the first and second dialysate fluids to substantially limit the contact between the blood fluid and the surfaces of the dialysis channel.

Figure 1:
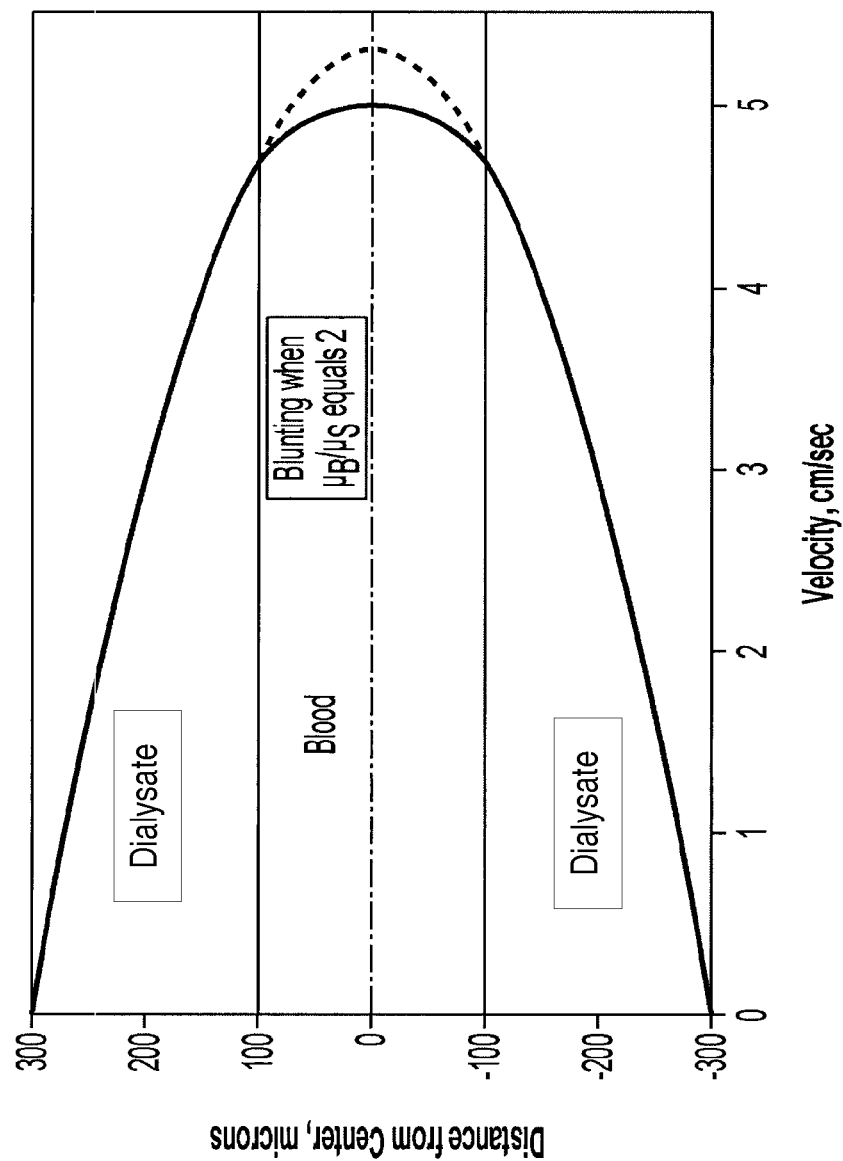
FIG. 1 shows the velocity profile of a core stream of blood sheathed on both of its sides by a dialysate fluid calculated for blood with a viscosity assumed twice that of the dialysate fluid and with a centerline velocity of 5 cm/sec.

Referring to FIG. 1, calculated for blood with a viscosity assumed twice that of the sheathing fluid and with a centerline velocity of 5 cm/sec, a flow path length of 10 cm would result in a contact time of slightly longer than 2 sec. The steady contact of two moving liquids for an exposure time determined by the length of their contact area divided by their interfacial velocity ($\tau=L/v$) is highly analogous to the sudden exposure of one volume of stagnant fluid to another for a specified time. Thus, what happens to the flowing fluids along their shared flow path is comparable to what would happen to two stagnant fluids over their exposure time to each other. The stagnant fluid problem was solved by Loschmidt in 1870.

$$E = \frac{1}{2} - \frac{4}{\pi^2} \sum_{0}^{\infty} \frac{1}{(2n+1)^2} \exp\left[-(2n+1)^2 \left(\frac{\pi}{2B}\right)^2 Dt\right]$$

for which the zeroth order term, $$E = \frac{1}{2} - \frac{4}{\pi^2} \exp\left(-\left[\frac{\pi}{2B}\right]^2 Dt\right),$$

suffices when $$\left(\frac{\pi}{2B}\right)^2 Dt > 0.7.$$

This formula greatly simplifies the estimation of how much mass can be transferred between fluids in a membraneless system. In particular, this formula provides an approximation of the extraction E of a component with a diffusion coefficient D when two liquids flow side-by-side and remain in contact for an interval of time, t.

Figure 2:
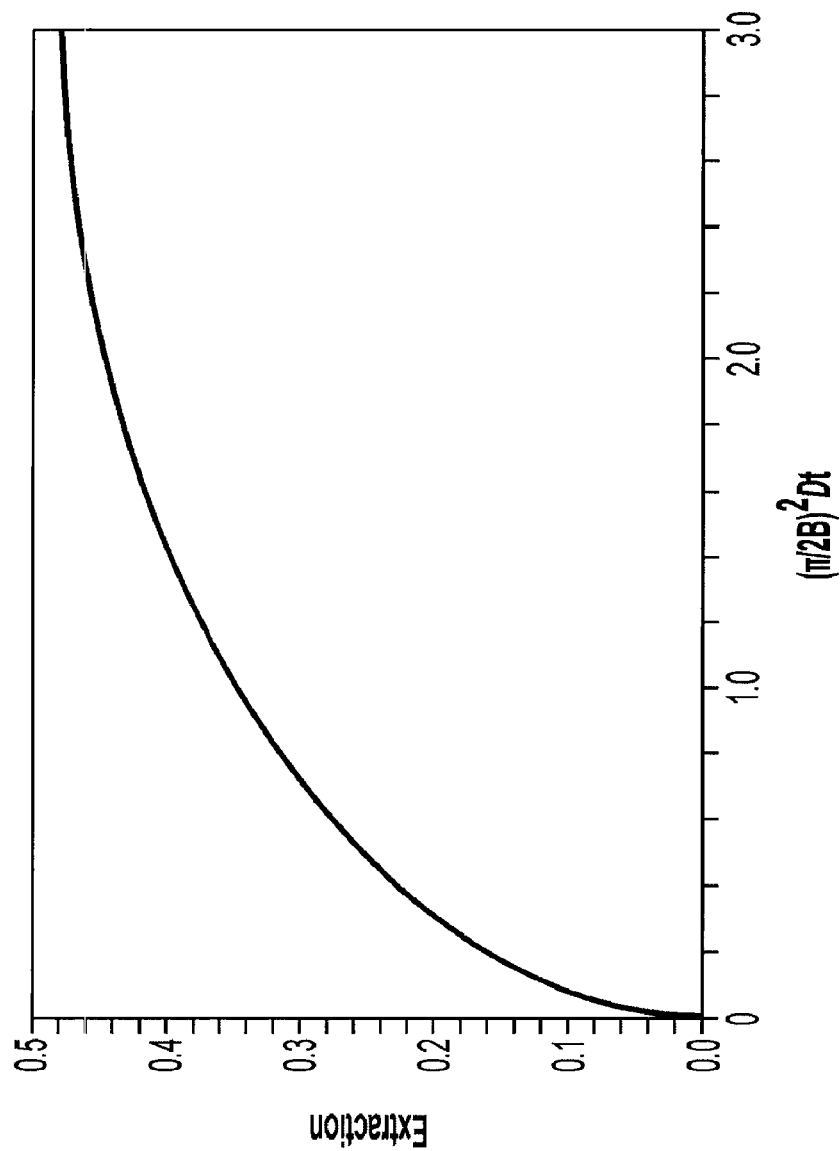
FIG. 2 shows a plot using Loschmidt's formula of 1870, where each fluid layer has the same thickness.

FIG. 2, meanwhile, shows a plot using a version of Loschmidt's formula, where each fluid layer has the same thickness B (i.e., B is the half-thickness of the sheathed layer of sample fluid). The situation shown in the plot of FIG. 2 can be interpreted as a blood layer, of thickness B, contacting a layer of sheathing fluid (i.e., extractor fluid). The sheathing layer is presumed to be at zero concentration and E is the fraction of material in the blood layer that is extracted in a time t, where D is the diffusion coefficient of the extracted substance. If a layer of thickness twice B is bounded on both sides by fluid layers of thickness B, the formula still applies, as written. As indicated by this formula, E cannot exceed ½ since the prescription of concurrent flow allows, at best, the two fluids to come to equilibrium.

For example, if one prescribes 90% of maximum extraction (E=0.45), the ratio $Dt/B^2$ must be approximately 0.86. Any combination of diffusivity, layer thickness, and exposure time that produces this value will produce the same extraction. Moreover, it can be shown that the necessary area (2LW) to achieve this extraction equals 0.86 BQ/D, where Q is the blood (and sheath fluid) flow rate. Thus, for urea ($D=10^{-5}$ cm$^2$/sec) at a blood flow rate of 0.3 cm$^3$/sec, the required area is 2.57 B $10^4$ cm$^2$. If B is taken to be 100 μm, the required area is 257 cm$^2$. This flow corresponds to what might be needed in a wearable artificial kidney. If, instead, a conventional flow of 5 cm$^3$/sec were used, the required area would be 4300 cm$^2$. Thinner films, moreover, would require less area but would result in higher shear rates and pressure gradients. In terms of extraction, any combination of length L and width W that produces the requisite area is equivalent. (If one assumes D for albumin to be 5 $10^{-7}$ cm$^2$/sec, its extraction would be 0.116, 26% of that for urea, unchangeable at this extraction level for urea).

It should be noted that use of the Loschmidt formula with flowing systems introduces an incongruity that prevents precise estimation of mass transfer rates and clearances, given that it presumes that both fluids are moving at uniform velocity. In particular, it provides an excellent approximation for the sheathed fluid (blood), but ignores the nearly linear decay in velocity with distance from the interface in the sheathing fluid. Nevertheless, the Loschmidt formula is adequate for design purposes when the sheathing layer has a total thickness (2B) that is twice that of its half of the blood layer (as shown in FIG. 1), and thus a rate of flow nearly equal to its half of the central stream.

The shear-induced self-diffusion coefficient of cells, meanwhile, can be estimated by using the expression of Leighton and Acrivos (1987) for concentrated suspensions: $D_{particle} \propto \phi^2 a^2 \dot{\gamma}^2$, where $\phi$ is the particle volume fraction, $\alpha$ is the particle radius, and $\gamma$ is the shear rate. Then, the characteristic displacement of a cell can be expressed as $\Delta y \propto \sqrt{D_{particle} t}$. Choosing representative values for the layered flow system such that the cell volume fraction $\phi \approx 0.45/2 = 0.225$, the average radius a of the red blood cell$\approx$2.5 μm, and the average shear rate $\dot{\gamma}$ over the blood layer$\approx$3 to 28 s$^{-1}$ (based on an average velocity range of 0.5 to 5 cm/s), we calculate that $D_{particle} \sim 10^{-8}$ cm$^2$/s, which is approximately three orders of magnitude smaller than the typical diffusion coefficient of small solutes. Based on this value of the shear-induced diffusion coefficient (and assuming 10 sec of contact between layers), it is estimated that blood cells are displaced by a characteristic distance $\Delta y \approx 3$ to 9 μM from the central layer, depending on the choice of blood velocity and the concomitant shear rate. As explained in greater detail below, this low distance of cell migration away from the central layer facilitates the removal of cell-free portions of blood by the membraneless separators described herein.

It should be noted that, according to one aspect of the present invention, the removing of undesirable materials from a sample fluid occurs under conditions that prevent advective mixing of blood and the secondary fluid. In its general usage herein, advection is used to describe the transport of fluid elements from one region to another, and is used to distinguish disordered convection from diffusion unaided by convection or diffusion in the presence of only ordered and unidirectional convection. The term advection is therefore used to mean a form of transport within a fluid or between two contacting miscible fluid in which clumps of fluid from two different positions are effectively interchanged. Advection, so defined, can occur in turbulent flows or in unstable laminar flows. Advective mixing, moreover, is often purposefully induced by the application of a moving agitator blade to a fluid. The prevention of advective mixing and the short contact times that lead to small areas of contact (and, in turn, to a small device that has a small size and a limited extracorporeal blood volume) is greatly facilitated by the use of a microfluidic geometry. An increase in channel height raises requisite contact time and tends to reduce the stability of the sheathed flow. When total blood layer thickness is 25, 50, or 100 μm, and the blood flow is 20 ml/min (as it might be with a wearable artificial kidney), the interfacial area needed to cause a substance such as urea ($D=10^{-5}$ cm$^2$/sec) to reach 90% of equilibrium is, respectively, 18, 36, and 71 cm$^2$.

As mentioned above, the devices, systems and methods of the present invention allow the purification of blood without the use of a membrane by contact of the blood with a miscible fluid under conditions that prevent advective mixing. It will be clear from the detailed description of various embodiments of the invention provided below that the invention is useful in hemodialysis, for example. However, it should also be noted, and understood by those skilled in the art, that the present invention is also useful in other situations where a sample fluid is to be purified via a diffusion mechanism against another fluid (e.g., an extractor fluid).

According to the principles of the present invention, the purification techniques described herein enable the flow of blood, completely or partially surrounded by another liquid (e.g., extractor fluid) such that the streams are contacted in a small channel and are subsequently separated at the end of the channel. The middle stream is, thus, the blood to be purified, while the surrounding stream (or streams) is the extractor fluid. This membraneless contact, or sheathing of blood with layers of a miscible fluid, according to principles of the present invention, may occur along a flow path whose cross-section is either rectangular, preferably of great breadth and limited thickness, or circular. The invention is not limited in this manner.

Persons skilled in the art will appreciate that the requisite transport areas, moreover, can be achieved by combinations of channel length, width, and number according to the principles of the present invention. In particular, Area=2 (top and bottom)×width×length×number of channels stacked or otherwise arrayed in parallel. (As used herein, the term "width" refers to a dimension perpendicular to the direction of flow and parallel to the interface between the two liquids, while, as explained above, the term "height" refers to a dimension perpendicular to the direction of flow and also perpendicular to the interface between the two fluids). It is shown herein that the competing requirements of small height (to avoid excessive diffusion times and in-process volumes), short length (to avoid excessive pressure drop) and practical limitations on width of a single device, which suggests the need to array them in parallel, side-by-side or in a stack can be satisfied in practical microfluidic devices.

Figure 3:
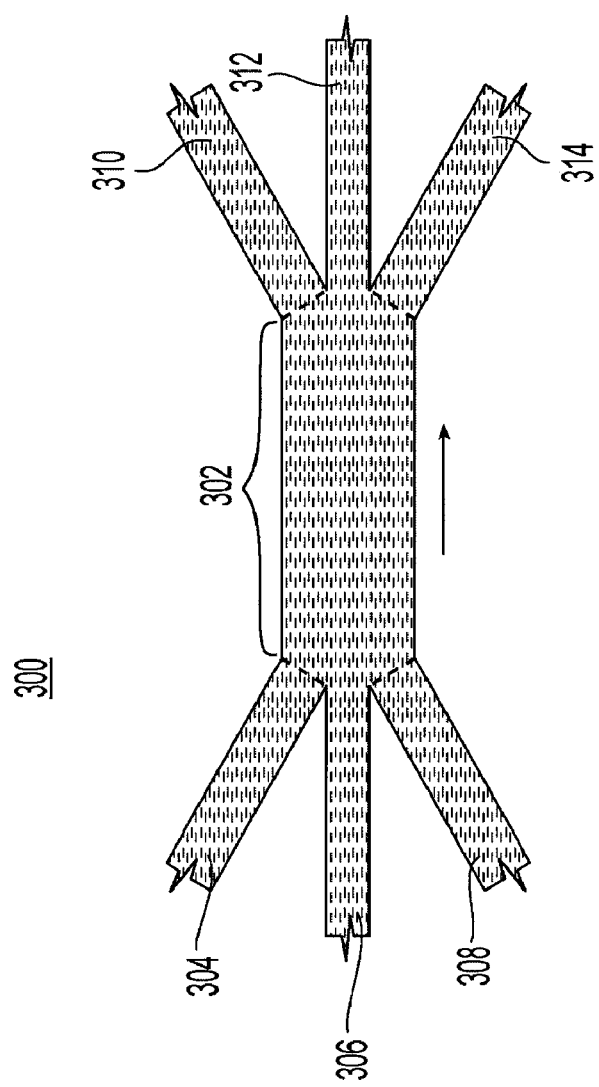
FIG. 3 shows a simplified view of a membraneless separator constructed in accordance with the principles of the present invention.

FIG. 3 shows a simplified view of a membraneless separator 300 fabricated in flat-sheet configuration in accordance with the principles of the present invention. According to one embodiment of the present invention, three flat strips of copper foil, each three centimeters wide, four centimeters long and 100 microns thick, are soldered in their mid-sections to form extraction channel 302. The ends (one centimeter) of the outer pieces are bent 30 degrees outward to form three separate inlet channels 304, 306 and 308 and three corresponding exit channels 310, 312 and 314 as shown in FIG. 3. According to the invention, the pieces are then coated with a mold release agent, and the channel is then placed in a Petri dish. At this time, an amount of PDMS precursor/curing agent mixture (10:1 ratio), sufficient to form a two centimeter-thick polymer layer after curing, is poured into the dish. After curing, the foil assembly is easily released from the PDMS replica, and the replica is sandwiched between two partially cured flat pieces of PDMS and annealed to form a well-sealed channel. Finally, slight vacuum is applied during the annealing to remove air bubbles trapped between the flow channel module and the flat pieces, and the sealed separator 300 is then ready for use (preferably after the chip is rinsed with ethanol and with de-ionized water, and then dried with compressed nitrogen gas). A flat piece of PDMS which served as a cover to seal the chip by adhesion is also preferably cleaned and dried in the same manner.

It will be understood that the particular fabrication process described above is for purposes of illustration only. For example, the dimensions of membraneless separator 300 may be altered without departing from the scope of the present invention. Additionally, for example, it will be understood that other fabrication processes not described may also be employed.

Figure 4:
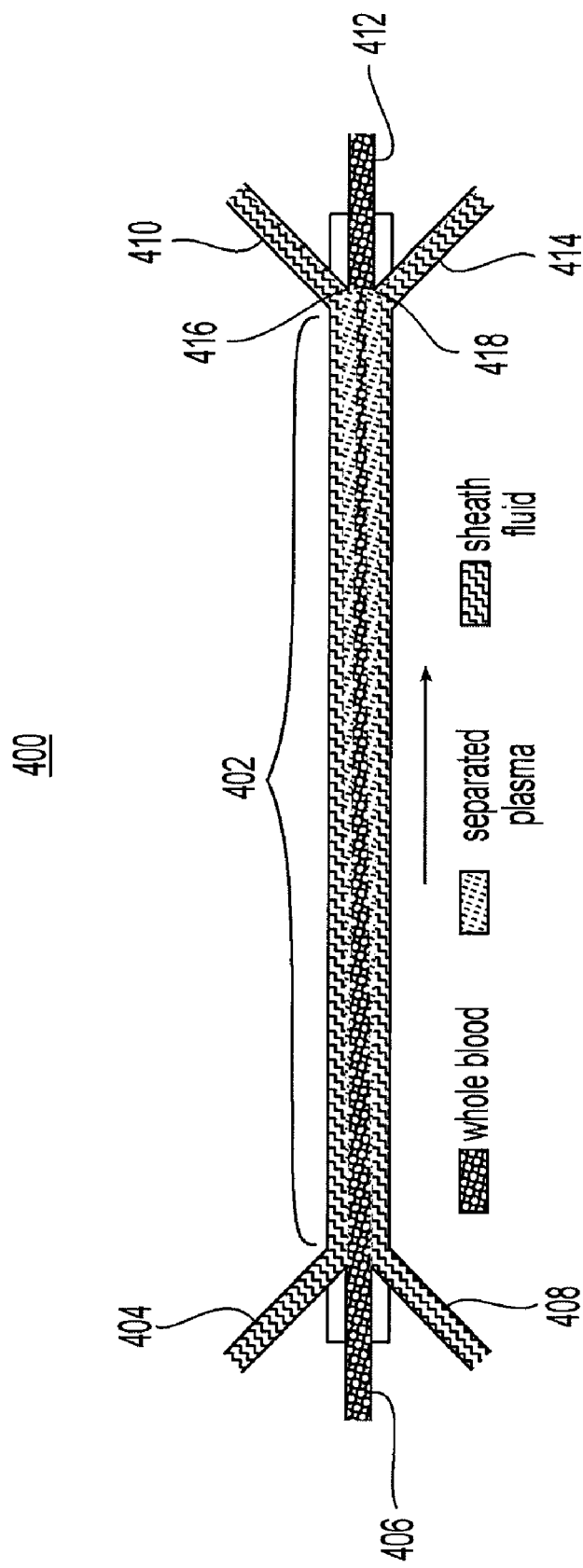
FIG. 4 shows a membraneless separator used for the purpose of plasmapheresis in accordance with the principles of the present invention.

FIG. 4 shows a membraneless separator 400 according to the principles of the present invention. Similar to separator 300 described above, separator 400 includes an extraction channel 402, three separate inlet channels 404, 406 and 408 and three corresponding exit channels 410, 412 and 414. As also shown in FIG. 4, a first diverter 416 is formed from portions of exit channels 410 and 412, while a second diverter 418 is formed from portions of exit channels 412 and 414. It will be understood, however, that the invention is not limited by the number of exit channels (or inlet channels) that are used, nor is the invention limited by the number of diverters formed therefrom.

As illustrated in FIG. 4, membraneless separator 400 can be used as a plasmapheresis device in accordance with the principles of the present invention. For example, as shown in FIG. 4, plasma from the blood entering extraction channel 402 through inlet channel 406 is skimmed and exits with sheath fluid through exit channels 410 and 414. This process of skimming is explained in greater detail below in connection with FIG. 7. In the case of plasmapheresis, the secondary separator is not needed since the product can be taken directly from the sheath fluid. However, not all of the sheath fluid can be taken, since a substantial fraction must be recirculated to the input of the primary separator.

Figure 5:
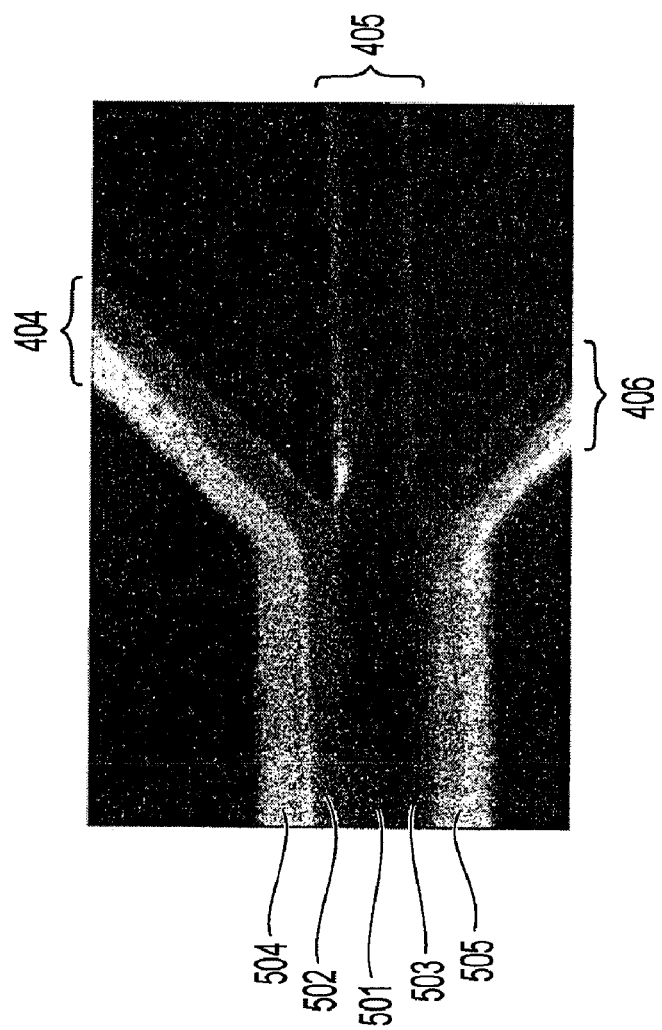
FIG. 5 shows the image of a portion of the membraneless separator of FIG. 5 while plasma is being skimmed from blood, as obtained by using a CCD camera.

FIG. 5, meanwhile, shows an image of the right-most portion of separator 400 shown in FIG. 4, as obtained by using a CCD camera (Sensys0401E, Roper Scientific). In particular, the image of FIG. 5 illustrates plasma being skimmed from blood according to the principles of the present invention. As shown in FIG. 5, a portion of the blood 501 provided through inlet channel 402 (not shown) exits through exit channel 405. Moreover, while cellular components of blood 501 migrate to the center (as explained below in connection with FIG. 7), cell-depleted (or cell-free) fractions of blood 501 such as plasma 502 and 503 combine with sheath fluid 504 and 505 to exit extraction channel 400 through exit channels 404 and 406, respectively.

It will be understood by persons skilled in the art that a membraneless separator as described herein is not intended to, nor could it, offer sufficient discrimination between the substances it is intended to remove and those it is intended to leave behind. Accordingly, for example, membraneless separators as described above will only function by themselves in the exceptional circumstance that all the components of plasma are to be removed. For example, a membraneless separator may be used alone when the removal of plasma, usually not in its entirety but without discrimination among its components, is to be removed, and the cellular components of blood are to be left behind.

Figure 6:
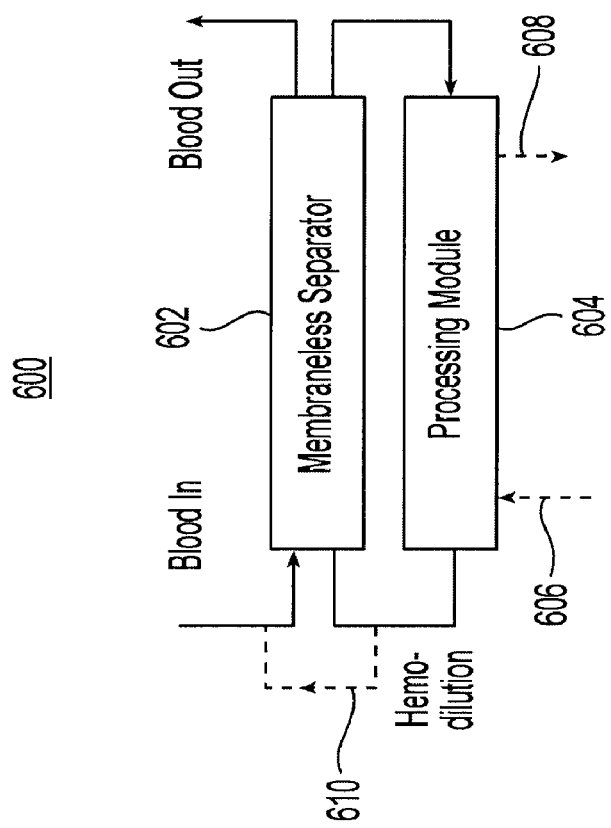
FIG. 6 shows a simplified block diagram of a system including a membraneless separator and a secondary separator in accordance with the principles of the present invention.

In all other circumstances, according to the principles of the present invention, a membraneless separator will operate in conjunction with a secondary separator that receives the sheath fluid and, optionally, a cell-depleted (or cell-free) part of the bloodstream. For example, to prevent the removal of macromolecules, the secondary separator can be used to generate a stream rich in macromolecules and free of small metabolite molecules and middle molecules that is recycled in sheath fluid to the membraneless separator. Thus, according to the invention, the secondary separator regulates the operation of the membraneless separator through the composition of the recycle stream that it returns to the inlets for sheath fluid of the membraneless separator (as shown in FIG. 6 and described in greater detail below). It should be understood that the secondary separator may incorporate a variety of means to remove solutes whose extraction removal from the circulation (i.e., the recycle stream) is desired, and that the invention is not limited in this manner.

One substance whose transport (i.e., removal from blood being processed) is typically undesirable is albumin. In each pass through an exchange device according to the invention, for example, albumin would be removed at more than ¼th the rate of small solutes, and albumin (which is confined to the blood space of an animal) would undergo perhaps 10 times as many passes as would urea which is distributed throughout the total body water reservoir. Thus, the fractional removal of albumin, even though its inherent diffusivity is smaller, would exceed the fractional removal of urea. According to the principles of the present invention, therefore, a secondary separator (e.g., a membrane device that permits extraction of urea and water but not albumin) may be used to recycle albumin to the blood. In particular, the sheath fluid received from the recycle stream will be depleted of urea and water, but will be rich in albumin. Thus, the composition of this stream will recruit the further extraction of urea and water but will not recruit further extraction of albumin, given that the difference in albumin concentration between the blood being processed and the sheath fluid will have disappeared.

It will be understood that an important specification of how the membraneless separator operates is the difference between the inlet flow rate and the outlet flow rate of the sheath fluid. For example, when these flows are equal and urea and water are removed by the secondary separator, there will be, at first, an insufficient transfer of water from blood to the sheath fluid to keep up with water removal in the secondary separator. Thus the concentration of proteins, including albumin, will rise in the recycle stream. When this concentration has reached a sufficiently high level, water transfer will be enhanced by a difference in protein osmotic (oncotic) pressure between the blood and the sheath fluid. Thus, the membraneless separator will balance its performance to that of the secondary separator. On the other hand, if the rate of withdrawal of sheath fluid is greater than its rate of supply, sufficient water may be sent to the secondary separator to keep up with its rate of water removal, but protein concentration will rise again until a concentration difference exists in the membraneless separator between the sheath fluid and the blood, causing a diffusion of protein back into the bloodstream. Once again, the membraneless separator will balance its performance to that of the secondary separator.

For example, when the principal goal of the treatment is the removal of highly diffusible (in general, low molecular weight) molecules, assuming a flow of 20 mL/min flow, the contact area in the membraneless separator will be in the range about 17 to 71 cm$^2$. When the principal goal of the treatment is the discriminating removal of slowly diffusible molecules (e.g., proteins and especially immunoglobulins), the contact area in the membraneless separator will be larger, in the range of approximately 1,700 to 7,100 cm$^2$ (assuming a flow of 20 mL/min), and the secondary separator will be configured to remove these molecules and to recycle smaller molecules (e.g. albumin) (unless their simultaneous removal is desired). In another aspect of the invention, one can plasmapherese and then remove IgG's and return the remainder of the fluid to the bloodstream.

FIG. 6 shows a simplified block diagram of a system 600 including membraneless separator 602 and secondary separator 604 in accordance with the principles of the present invention. Although not shown in detail, it will be understood that membraneless separator 602 may be similar to those separators shown in FIGS. 3 and 4 and described above, for example.

According to the principles of the present invention, blood that is to undergo processing is provided to (and removed from) membraneless separator 602. Meanwhile, sheathing fluid that is recycled by secondary separator 604 is also provided to (and removed from) membraneless separator 602. As also shown in FIG. 6, whenever secondary separator 604 transfers solutes to a second fluid (e.g., dialysate), fresh dialysate connection 606 and waste dialysate connection 608 may be used for providing fresh and waste dialysate streams, respectively. It will be understood that shunting of fresh fluid directly to the blood stream, as represented by dashed line 610, is also a possible but not mandatory maneuver. In general, FIG. 6 makes the role of membraneless separator 602 clear: to equilibrate solutes of interest with the sheathing fluid without transfer of cells.

It will be understood that secondary separator 604 may use any of many available separation principles known to those skilled in the art, including ultrafiltration, sorption using a wide range of sorbents targeted to particular small and large molecules, chemical reaction, and precipitation. Plasma diafiltration (a variant of hemodiafiltration), for example, may also be used according to the principles of the present invention. The following international publications which refer to hemodiafilters are incorporated by reference herein: WO 02/062454 (Application No. PCT/US02/03741), WO 02/45813 (Application No. PCT/US01/47211), and WO 02/36246 (Application No. PCT/US01/45369). According to additional embodiments of the present invention, moreover, when low-molecular weight solutes are to be removed by plasma diafiltration, a stream of sterile buffer is added to the blood to allow a greater volume of fluid, with its accompanying small molecules, to pass through the diafiltration membrane. In conventional diafiltration, this volume may be added before or after the diafilter. In this invention, however, it is advantageous to add it either to the bloodstream or the recycle fluid from the secondary separator 604, which is the primary source of sheath fluid.

Figure 7:
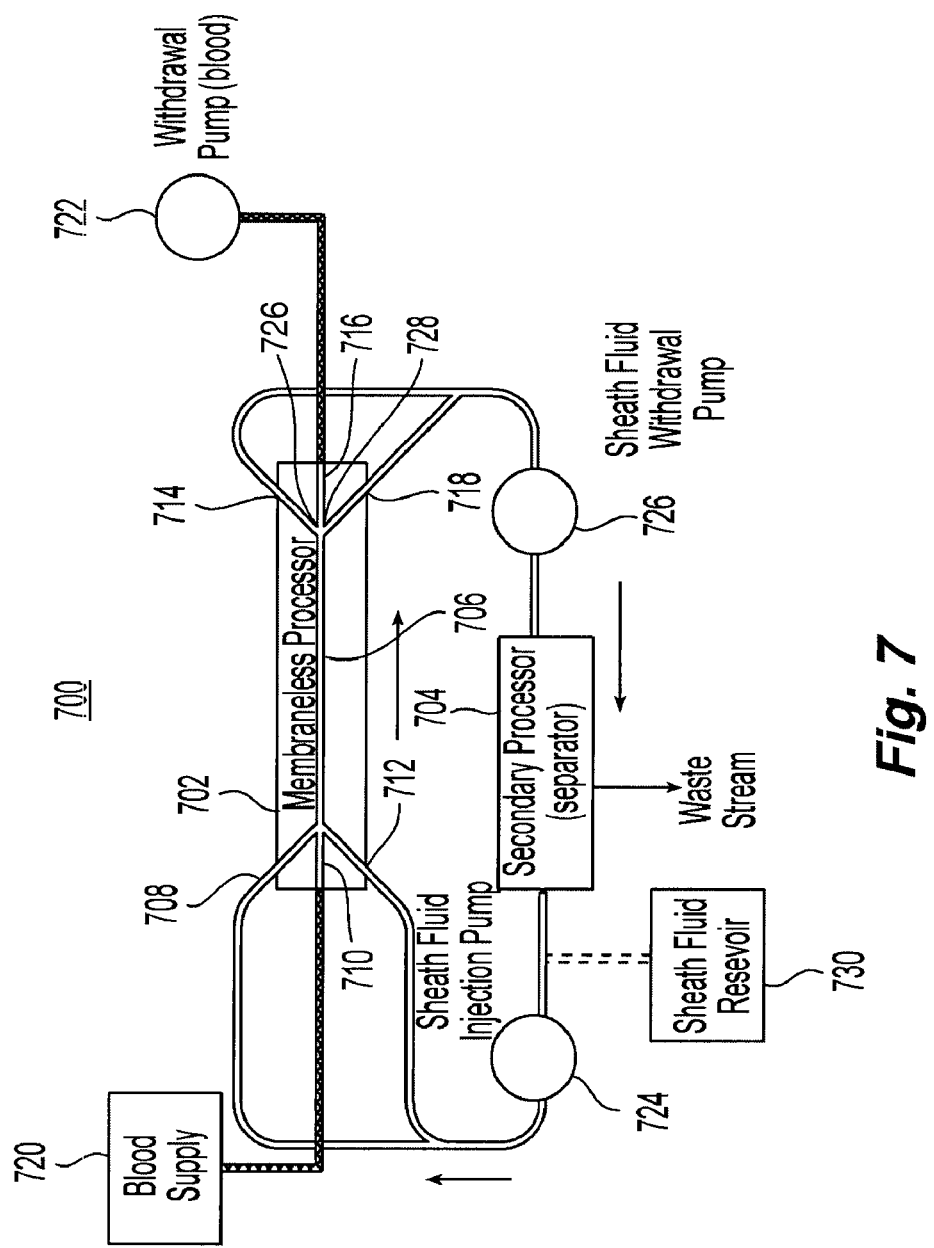
FIG. 7 shows a more detailed view of a system including primary and secondary separators in accordance with the principles of the present invention.

A more detailed view of a system 700 which includes membraneless separator 702 and secondary separator 704 in accordance with the principles of the present invention is shown in FIG. 7. As shown in FIG. 7, separator 702 includes extraction channel 706, inlet channels 708, 710 and 712 and exit channels 714, 716 and 718.

According to the principles of the present invention, system 700 also includes blood supply 720, and a plurality of pumps 722, 724 and 726 (which may be either manually or automatically operated, such as by using detection and regulation techniques described below). As shown in FIG. 7, blood supply 720 provides blood to be processed to membraneless separator 702 through blood inlet channel 710. It will be understood that blood supply 720 may be a living person or other animal, for example, or may be a blood reservoir. Blood withdrawal pump 722, meanwhile, is responsible for removing blood from separator 702 through blood exit channel 716.

As illustrated by FIG. 7, the flow of sheath fluid (or extractor fluid) into separator 702, through sheath inlet channels 708 and 712, is controlled by sheath fluid injection pump 724 (which preferably provides sheath fluid in equal parts to channels 708 and 712). The flow of sheath fluid out of separator 702, through sheath exit channels 714 and 718, meanwhile, is controlled by sheath fluid withdrawal pump 726 (which preferably draws equal amounts of sheath fluid out of channels 714 and 718). According to preferred embodiments of the present invention, pump 724 is a two-chamber pump that provides sheath fluid at equal velocities (and with substantially similar composition) to both inlet channels 708 and 712, while pump 726 is a two-chamber pump that removes sheath fluid from exit channels 714 and 718 at equal velocities. Moreover, it is also contemplated that pump 724 be replaced by two pumps (not shown) for separately providing sheath fluid to inlet channels 708 and 712, in which case the composition of the sheath fluid entering inlet channel 708 may be substantially similar to, or different from, the sheath fluid entering inlet channel 712. Similarly, two pumps (not shown) can be used in place of pump 726 for the purpose of separately withdrawing sheath fluid from exit channels 714 and 718. It is also contemplated that, in other embodiments of the present invention, sheath fluid entering through inlet channel 708 and exiting through exit channel 714 flows at a different velocity than the sheath fluid entering through inlet channel 712 and exiting through exit channel 718. The invention is not limited by the particular usage of pumps or sheath velocities described herein in connection with the description of FIG. 7.

As explained above, a membraneless separator according to the invention also needs two or more diverters to operate. (Four may be used when true sheathing is achieved, i.e. in sheath-blood-sheath configuration. In general, if n is the number of layers and there are inlet and outlet diverters, there can be 2(n−1) diverters.) Thus, according to the principles of the present invention, a first diverter 726 is formed from a portion of sheath exit channel 714 and a portion of blood exit channel 716. Moreover, a second diverter 728 is formed using a portion of blood exit channel 716 and a portion of sheath exit channel 718. It will be understood that, in embodiments of the present invention using more than two layers of sheath fluid, addition diverters will be used.

In certain preferred embodiments of the invention, the sheath fluid provided to separator 702 (from separator 704 and/or optional sheath fluid reservoir 730) by sheath fluid injection pump 724 occupies approximately ⅔ of the cross-section of extraction channel 706, with blood from blood supply 720 in the middle ⅓. In this manner, each half of the blood layer in extraction channel 706 is primarily affected by one of the sheathing layers, and the sheathing layers are traveling at an average velocity that is approximately half that of the blood (even though the interfacial velocities of the blood and sheathing fluids are equal). Thus, the volume of blood and the volume of sheathing fluid that pass through the unit in a given period of time are approximately equal. Although the invention is not limited in this manner, it should be noted that, in the configurations described here, efficiency drops when the volumetric flows of the two fluids (i.e., blood and sheath fluid) are very different from each other.

In order to cause the separation (or skimming) of all or part of the cell-depleted component of the blood being processed, according to various embodiments of the present invention, the inlet and exit flows of the sheath fluid are controlled (via pumps 724 and 726, respectively) such that more sheath fluid is withdrawn from separator 702 than is provided thereto. For example, it is possible to skim 10% of the blood flow by running sheath fluid withdrawal pump 726 at a rate that is 10% higher than the rate of sheath fluid injection pump 724. It will be appreciated that, when this is done, the blood efflux rate is determined and need not be controlled, as it should naturally have an outflow that is 90% of the inflow.

As explained above, when indiscriminate plasma removal is not desired, the plasma that is skimmed from the blood using membraneless separator 702 is processed by secondary separator 704, which regulates the operation of separator 702 through the composition of the recycle stream that it returns to sheath inlets channels 708 and 712 (i.e., a recycle stream is used to limit transport of blood components for which extraction is not desirable). According to the principles of the present invention, a substantial benefit arises because secondary separator 704, whether membraneless or not, is able to achieve high filtration velocities due to the fact that concentration polarization is limited to proteins and does not involve cells. Moreover, because cells are retained in the membraneless separator 702, they would see artificial material only on its conduit surfaces, not on its liquid-liquid contact area, with the result being a reduction in bioincompatibilities and a reduced (or eliminated) need for anticoagulation. Additionally, because the primary transport surface in the system is intrinsically non-fouling, a major deterrent to long-term or continuous operation is removed, opening the possibility of a wearable system with the recognized benefits of prolonged, slow exchange.

It should be understood that any operation of membraneless separator 702 that allows the sheath exit flows to be larger than the corresponding inlet values will induce a convective flow from the blood stream, over and above the diffusive flow. In order to prevent such a convective flow from carrying blood cells with it (as would be the case if the distribution of cells in the blood stream was uniform), it is important that cellular components of the blood have migrated to the center of the blood stream in order to permit significant plasma skimming. As should be appreciated by those skilled in the art, centripetal drift of cells occurs under a variety of flow regimes. According to the invention, therefore, various flow conditions can be used that cause blood cells to move away from the blood-liquid interface. For example, when blood flows in a tube below a wall shear rate (measured as the blood-flow velocity gradient perpendicular to the tube wall) of about 100 reciprocal seconds, this shear rate causes cellular components to migrate the center and leave the sheath as cell-free, essentially pure plasma. (See Goldsmith, H. L. and Spain, S., Margination of leukocytes in blood flow through small tubes, Microvasc. Res. 1984 March; 27(2):204-22.)

It will be appreciated that long-term stability is necessary for satisfactory operation of the microfluidic devices described herein. For example, it is desirable to prevent inappropriate splitting of an exit stream which, uncorrected, could result either in loss of cells or unintended infusion of sheathing solution into the bloodstream. Moreover, the presence of blood cells in the sheath, or extractor fluid may also be undesirable. According to another aspect of the present invention, therefore, on-board electronics and photonics (not shown), which are common features of chip-based microfluidic devices, may be used. In particular, such electronics or photonics could be used to regulate system 700 (i.e., to introduce flow changes) with an electrically activated device (e.g., a piezoelectric valve) that is mounted on the same plate, or "chip," on which separator 702 is located.

According to one embodiment of the invention, for example, very low concentrations of cells would be permitted and monitored (e.g., before or after the sheath fluid being provided to secondary separator 704) by using any suitable detector, such as a photo detector. An ultramicroscope (a light-scattering device that is particularly sensitive in showing the presence of dilute particles) is one example of a photo detector which can be used. Based on this monitoring, flow corrections that would provide the system with long-term stability can be made which include, for example, adjusting the blood-sheath fluid interface. In particular, by adjusting the flows to separator 702 to reposition the interface, desired components can be retained in the blood. For example, when an excessive number of blood cells is present, the flow of blood could be decreased (or the flow of extractor fluid increased) in order to shift the blood-sheath fluid interface accordingly.

Additionally, according to another aspect of the invention, on-board electronics can be used to protect against the type of flow imbalances that might cause large blood losses in one direction or massive hypervolemia in the other direction, which are naturally prevented when a membrane is present but which may occur in a membraneless device. It will be understood by those skilled in the art this type of detection and regulation may also be used in conjunction with the other embodiments of the present invention described above.

As explained above, in all membraneless contact configurations, the fluids (e.g., blood and sheath fluid) must flow in the same direction and at the same rate wherever they are in contact. In particular, any discrepancy in magnitude or direction of the two flows, wherever they meet, must disrupt the blood-fluid interface and induce undesirable advection. Moreover, since the fluids must flow in the same direction, the most that can be accomplished in one membraneless unit according to the invention is the equilibration of the sheath and blood streams (which, according to Loschmidt's formula provided above, means that if the sheathing fluid is flowed at the same rate as blood, the extraction E of a solute cannot exceed ½). In other words, if the two flows are equal, at most half of any solute can be transferred. Moreover, while greater flows permit larger fractions, E, of a solute to be removed, they require higher circulation rates to the secondary separator and thus force processing of solutes at lower concentrations, which is generally undesirable. Therefore, it is generally desirable for these flows to be nearly equal, within at least a factor of 2 or 3.

This limitation on extraction can be largely overcome, however, by the configurations shown in FIGS. 8 and 9 and described below which achieve the effect of opposing flows (counterflow) by the juxtapositions of modules. In particular, low extraction efficiency can be overcome by more sophisticated layouts of a microfluidic system such that flows are concurrent in each unit of the system, but the overall flow approaches countercurrency in pattern and efficiency.

According to the invention, subdivision of a given, desired contact area into n units each connected to the other in a countercurrent manner, even though the flow within them is concurrent, is used to allow extraction efficiency to rise. Thus, if an area were divided into four units, for example, and each had an extraction efficiency of 50%, the composite unit would have an efficiency of 0.8 or 80%.

Figure 8:
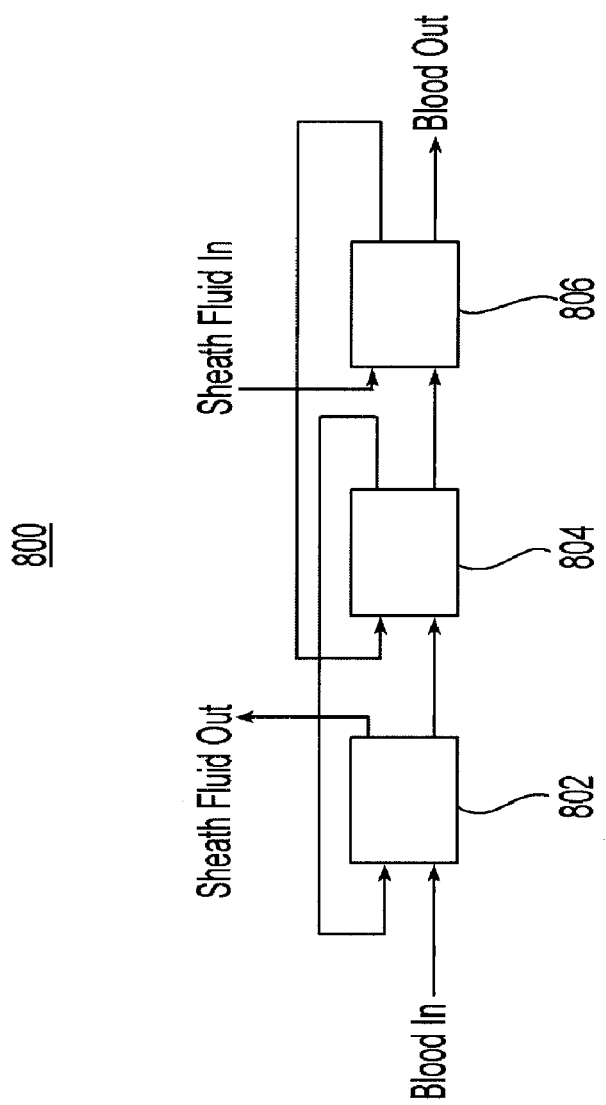
FIG. 8 shows the configuration of a system subdivided into three units in accordance with the principles of the present invention.

FIG. 8 shows the configuration of a system 800 according to the invention in which the total area of contact is partitioned into three sub-units 802, 804 and 806 (i.e., n=3). In operation, blood to be processed is first provided to sub-unit 802, then passes through sub-unit 804, and finally, exits out of sub-unit 806. The sheath fluid to be used in system 800, on the other hand, is first provided to sub-unit 806 (at this point, the sheath fluid has no blood components). The sheath fluid exiting sub-unit 806 is next provided to sub-unit 804, and after exiting sub-unit 804, is provided to sub-unit 802. Thus, assuming each unit has an extraction efficiency of 50%, the overall extraction efficiency of the composite unit, $E_O$, is equal to 0.75 or 75%. Accordingly, it becomes possible, at equal flows, to remove 75% rather than only 50% of the solute of interest. In will be understood that the extraction efficiency approaches 1.0 or 100% as the number of small units approaches infinity. Persons skilled in the art will appreciate that, although not shown, the sheath fluid exiting sub-unit 802 may be provided to a secondary separator as described above. Moreover, while three sub-units 802, 804 and 806 are shown in FIG. 8, it will be understood that any number of sub-units (e.g., 2, 4, 5, etc.) may be used in system 800, all of which may be easily introduced on a master chip fabricated according to well known techniques for the general fabrication of microfluidic devices.

Figure 9:
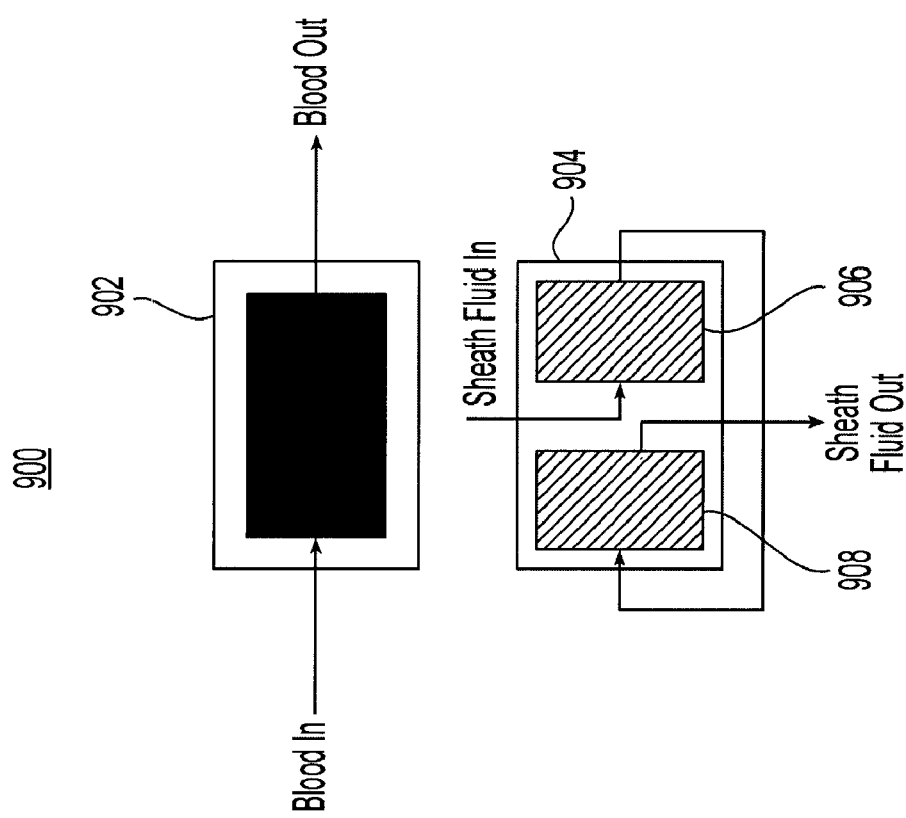
FIG. 9 shows the routing of fluids between separate units in accordance with the principles of the present invention.

FIG. 9 shows another example of a system 900 using sub-units according to the principles of the present invention. In particular, FIG. 9 shows two flow patterns 902 and 904 that would be superimposed on each other in a single cartridge. For example, the top could represent blood, while the bottom could represent an extractor fluid (e.g., dialysate). As shown in FIG. 9, sheath fluid flows through sub-unit 906 prior to flowing through sub-unit 908. In this manner, with sufficient contact area, the fraction of material in the blood layer that is extracted will be equal to $\frac{2}{3}$ or 67%.

Persons skilled in the art will appreciate that many different fabrication techniques can be used in accordance with the principles of the present invention. In recent years, controlled fluid movement and transport among fluids has been achieved in very small channels and at very low rates of flow largely for the purpose of assaying the contents of a minute fluid sample in order to determine, for example, the catabolite concentration in the blood. These devices have been enabled by recently developed microfabrication methodologies. The Holy Grail has been the development of a "Lab on a Chip," in which several sequential analytical processes are conducted on a single chip that may be, for example, one square centimeter in area. Transport of a chemical or biochemical sample from one process to another and on and off the chip itself requires fluid handling capabilities, and thus, this enabling technology is commonly called "microfluidics." Microfluidics is essential for nearly all on-chip applications. The synthesis of chemicals in microfluidic geometries is an application that is perhaps closer in concept to the scope of this disclosure because of the need to process a relatively larger amount of fluid. Synthesis includes, perforce, the separations needed between the steps of a chemical reaction sequence. While the aims of synthesizers differ from ours, and embrace some issues that we do not now see as pertinent, all of this work, reported and emergent, is of interest. Specifically, the present invention embraces some of the fabrication techniques and experimental methods developed for the fabrication and characterization of microfluidic device structures, to define upwardly scalable transport to and from blood.

According to the invention, moreover, microchannel structures for flow experiments may be formed by a rapid-prototyping technique. For example, the required structures may be realized in PDMS (silicone) resin by replica-molding from master structures created in thick negative photo resist (SU-8) by optical lithography. Commercially available, standard grade mixtures of EPON SU-8 photo resist, SU-8-5 (52% solids), SU-8-25 (63% solids), SU-8 50 (69% solids) and SU-8 100 (73% solids), for example, may be spun onto Si wafer substrates at a speed of rotation that depended on the film thickness needed, yielding films that were 10 to 300 μm thick. For example, SU-8 50 spun at 1100 rpm yields a 100 μm film. Prior to exposure, moreover, the spun layer is preferably baked on a precisely leveled hot plate at 95° C. for a time that is dictated by the film thickness (ranging from minutes to hours). These samples are then allowed to cool before further processing. Post-bake exposure, meanwhile, can be done using a direct laser writing system. The photolithographic setup consists of an Ar-ion laser (wavelength $\lambda$=350 nm), focusing optics, and a computer controlled sample stage. The movement of the stage along all three axes (x, y, z) is achieved by stepping motors. Desired master patterns were created by translating the samples underneath the focused laser beam to expose the outline, and then scanning across the interior so that the intended micro channel was fully exposed. Dynamical focus correction or the sample tilt with respect to the scanning laser beam was the done by on-the-fly adjustments of the distance between the focusing lens and the sample stage. In a preferred embodiment, this exposure is carried out at 95° C. for 15 min. Development, meanwhile, can be carried out in a commercial SU8 developer, again for a time based on film thickness (with the sample being lightly stirred during development). Patterns created in SU-8, meanwhile, are used as molding masters for replication in PDMS. PDMS is prepared from a mixture of PDMS precursor and curing agent (Sylgard 184 kit, Dow Corning) in a 10:1 ratio by weight. Before curing, the mixture is placed in vacuum to evacuate bubbles formed during mixing. It is then poured over the SU-8 master, which had been previously coated with a thin layer (~50 nm) of chromium to improve the release of the PDMS casting, after curing. Curing is done at 70° C. for approximately twelve hours. Once the SU-8 film is spun, pre-baked and cooled as described above, a Karl Zeiss MJP3P Contact Mask Aligner can be used for exposure, together with standard chromium masks or transparency masks depending on the resolution required. The films are then post-baked, and developed in the manner outlined in the previous section. The same pattern transfer technique is used to produce PDMS replicas.

It is apparent to those skilled in the art that many advantages may be provided in the various embodiments of the present invention described above. For example, the devices, systems and methods according to the principles of the present invention are capable of diffusing various blood components having different sizes, including 'small' molecules, 'middle' molecules, macromolecules, macromolecular aggregates, and cells, from a blood sample to the extractor fluid. This ability is particularly important considering the fact that different treatments require the removal of different sized particles. For example, in dialysis, one may desire to remove molecules of low molecular weight, while in the treatment of acute liver failure, both small and intermediate-sized molecules are to be removed. In therapeutic apheresis, meanwhile, one generally wishes to remove selected protein macromolecules (e.g., immunoglobulins), while in the treatments for fulminating sepsis, it is toxins of intermediate molecular weight that one generally desires to remove. On the other hand, in proposed anti-viral treatments, one wishes to remove free viral particles, while in the treatment of congestive heart failure, one simply wishes to remove water.

It should also be apparent that a device or system according to the invention may be used to process the blood of a single individual for the purpose of treating any of a large number of disease states. For example, therapies according to the invention may be used in the treatment of acute renal failure, acute liver failure, high antibody levels in myasthenia gravis and other autoimmune diseases. Additional uses include, for example, the removal by either precipitation or sorption of LDL in homozygous hyperlipidemia, in addition to the removal of malignant sepsis or fluid in cases of congestive heart failure, for example. The invention may also be used to aid in the reduction of viral burdens in AIDS patients, as well as for treatment of patients requiring other types of blood purification. Patients with diabetes, patients that have suffered a drug overdose, patients that have ingested a poison, patients suffering from renal failure, patients suffering from acute or chronic liver failure, or patients that have Myasthenia gravis, lupus erythematosis, or another autoimmune disease may also benefit from the devices and systems of the present invention. For example, while an exchange device according to the invention is not a cure for diabetes, it can be useful in the amelioration one or more symptoms of diabetes. Moreover, the device or system of the invention could be useful in clearing the blood of IgG molecules or other molecules, which are causative of an autoimmunity disorder. Additionally, the device or system of the invention can be used in acute dialysis or for extended dialysis. There is an advantage to a system that easily separates plasma from cells, that permits another system to dehydrate (remove water from) the plasma in the absence of cells, and then let the transformed (extracted, reacted, etc.) plasma return. One skilled in the art will also appreciate that patients (or animals, in the case of veterinary use of the present invention) suffering from disorders, diseases and syndromes not listed herein may nonetheless be included in the patient pool intended for the device and system according to the invention.

Additionally, because the membraneless devices and systems described above have a small need for supporting machinery, and may be expected to be much smaller, to avoid high cell concentrations and membrane contact, and to operate throughout at low rates of shear, they are especially compatible with cognate processes. In one embodiment, a wearable (or at least portable) system according to the invention can run between 20 and 24 hours per day at a flow rate of about 20 cc/min, for example. The patient could then have, for example, 4-5 hours each day without the device in place which could be used for personal hygiene (e.g., showers or baths), sports activities, or other activities not amenable to the small system being worn or used. The dialyzer should always be in place and may require protection from aquatic environments. By accepting the constant presence of the small device, a patient avoids the pain, risk, and treatment-limiting issues associated with inserting and removing needles or other blood access connectors. The patient is able to hook up and detach to the device at will and painlessly, however he/she would have to carry the core device with him/her. In one embodiment, the daily or nocturnal dialysis may require active interference with the circulation. The invention thus addresses a problem recognized by the dialysis community (i.e., the negative side effects such as physical exhaustion, thirst, etc. associated with an episodic dialysis schedule), for which daily or nocturnal hemodialysis is not always a sufficient alternative. In particular, the invention described herein allows the patient to move about in a normal manner (e.g., go to work, school, home, etc.) while being subject to ongoing dialysis.

In addition to the treatment of various disease states, a device or system according to the invention may also be used for extracting blood components that are useful in treating others, as well as for purposes of studying the processes by which molecules and cells segregate and diffuse in blood. For example, it is known to those skilled in the art that diffusion of individual molecular species in blood may not occur independently and may not depend on size in the simple manner dictated by the Stokes-Einstein equation. Moreover, many solutes may partition into multiple forms: free, in complexes, bound to plasma protein, bound to cell-surface moieties, or as intracellular solutes. Relative to the rate of diffusion of the solute, its different forms may or may not be in local equilibrium. These phenomena are likely obscured when a membrane is present because it slows and controls overall transfer rates. Therefore, a membraneless device or system according to the invention can be a useful scientific tool to study these phenomena and a system in which rates are raised enough that partitioning may set limits on how much and how quickly a solute can be removed. A particular example is bilirubin bound to albumin. Another example is inorganic phosphorous which exists as partially ionized salts, as two anionic forms in plasma and in several intracellular forms.

A Membraneless Artificial Kidney Device Comprising A Flush Port—In one aspect of the invention, the membraneless device further comprises a flush port. In a membraneless artificial kidney, it is difficult to keep all blood cells from entering the sheath fluid. If the cells do enter the sheath fluid, it is likely that they will not return to the bloodstream before they have reached a prohibitive concentration, and there is no other method of egress. The invention provides for a flush port in the membraneless device. A sterile fluid is injected into the sheath fluid, flushing it and its contents into the bloodstream. The sheath fluid is thus replaced by clear, fresh fluid. This process may be conducted intermittently and at such intervals as not significantly to increase the overall volume of liquid to be removed from the blood.

Direct contact between uremic blood and a fluid capable of receiving uremic toxins is possible. Such contact by itself is, however, not beneficial because it depends on diffusion coefficients in blood to select the molecules that are removed. This selection is inadequate and would result in the exhaustion of a patient's albumin pool before useful reduction in the urea pool was achieved. Direct contact that is accomplished by sandwiching blood between two layers of a "sheathing" fluid, followed by diafiltration of the sheathing fluid through conventional membranes and recirculation of the sheathing fluid, is possible. This adaptation of membraneless transport of molecules from blood eliminates almost all contact of blood with solid artificial surfaces and the subsequent diafiltration and recirculation of the sheathing fluid allows precise control of what is removed from the system. Slightly hyperosmotic protein is carried back by the recirculating sheathing fluid. Only solutes and water that pass the diafilter, which operates on a cell-free fluid, are able to leave the system. The system depends strongly on the ability to keep cells out of the sheathing fluid. A quantitative design of a wearable dialyzer based on a circulating sheathing fluid is presented.

All biological transport between phases uses membranes. This is true at the submicroscale where each organelle of a cell possesses a membrane, as does the cell itself. It is true at all higher scales where we encounter the vascular endothelium, the alveolar membrane, the intestinal wall, and many epithelial surfaces. Faced with the prevalence of membranes throughout biological systems, one must ask the very serious question, why would one even attempt mass transfer from one fluid to another without a membrane? The answer to this question lies in the imperfections of man-made membranes: (1) A typical dialysis membrane is at least 1000 times thicker than its natural counterpart. (2) Its interface foments a largely inappropriate set of chemical reactions with blood components. (3) In long-term use it becomes fouled—clogged with molecular aggregates that impede transport.

A dialysis system is wearable and works as a dialyzer through which blood would flow constantly is provided by the invention. [1-7]. Such a device needs to be small, which means that its exchange rates between blood and dialysate need to be fast. Its blood-wetted surfaces should be highly biocompatible and should not require heparinization of the blood flowing continuously past them. Since the blood-wetted surface is essentially permanent, it should be much more resistant to fouling than any artificial membrane now known. These qualities could be obtained if it were possible to have direct, liquid-liquid contact of blood with dialysate. Membranes are important in systems because they do the following: (1) Membranes select—so that some molecules pass through them and others do not. In biological systems, transport without molecular selectivity at some point in the transport path is essentially useless. (2) Membranes offer a mechanical barrier that prevents gross mixing of two otherwise miscible fluids, and they permit the use of a pressure difference to extract water. (3) Membranes define the boundaries of different compartments.

The invention provides for a system that offers the advantages of both membrane-moderated and membraneless transport. In one aspect, the invention encompasses such a system devised as a wearable hemodialysis system.

Microfluidic-Membraneless Transport

Figure 10:
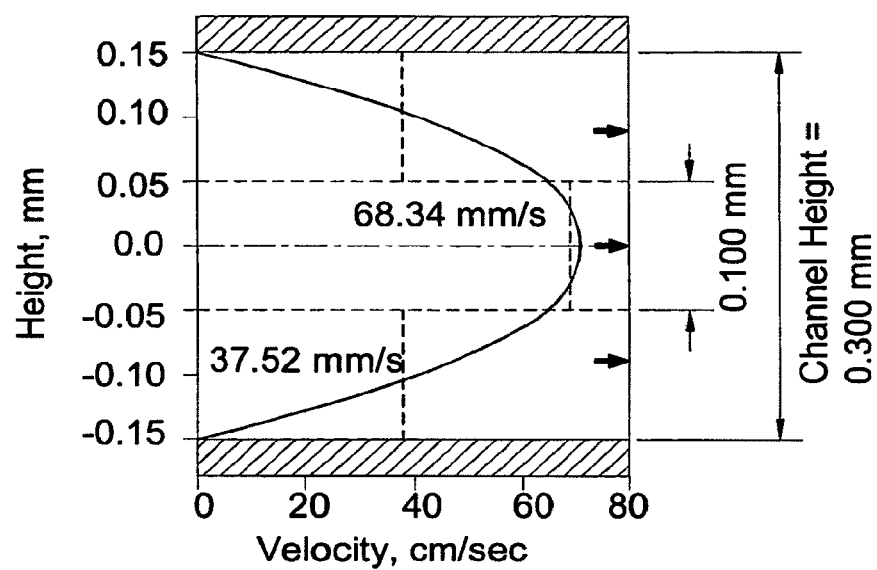
FIG. 10 is a diagram showing a cross-section of blood flowing at a mean velocity of 68.34 mm/sec, sandwiched between two layers of sheath fluid, each flowing at a mean velocity of 37.52 mm/sec. Each layer is flowing from left to right. Each layer is 100 micrometers (0.1 mm) thick. The blood layer is isolated from wall contact by the layers of moving sheath fluid and experiences a very low rate of shear, evidenced by its very flat velocity profile.

It has been know for many years that one fluid could be flowed beside another without convective mixing [8,9]. However, the concept became useful only with the advent of reliable means of microfabricating thin fluid channels, usually through the use of photolithographic and micromachining techniques that were developed first for manufacturing large-scale, integrated electronic devices on silicon chips. In the system considered here, the flow of three liquid layers are examined, each—nominally—100 μm thick. To a very good approximation the outer, sheathing layers will have a mean speed that is half that of the center (blood) layer (FIG. 10), so that, overall, the two liquids will have the same flow rate. Systems with different flow rates are possible but are generally less desirable. It is important to notice that the flows in direct contact must be in the same direction, as shown in FIG. 10. An attempt at counter- or cross-flow would lead to gross mixing of the streams.

Figure 11:
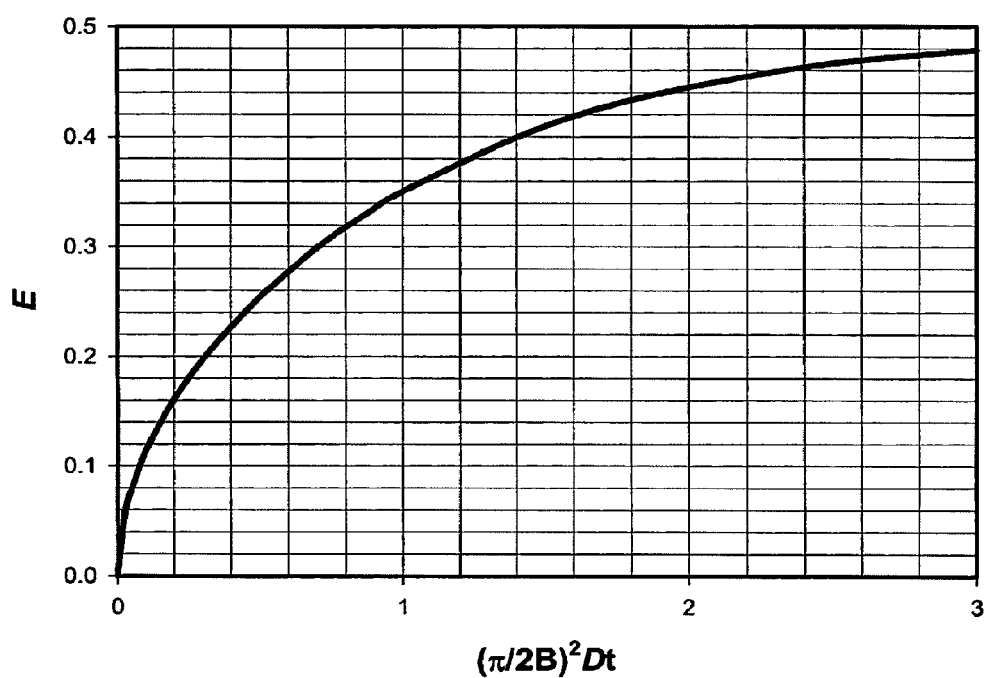
FIG. 11 is a graph showing Boltzmann's relationship expressed as extraction fraction, E, between two stagnant solute layers, each of thickness, B, as a function of time, t [18, 19]. The solute has a diffusion coefficient of value D. In the present paper we apply this result to a different but related situation: A central blood layer of thickness 2B diffuses into two sheathing streams, also of thickness, 2B. Each half of the blood layer feeds one of the two sheathing streams. The approximate calculations reported here assume that each half of the blood layer, whose thickness is B, equilibrates with the sheathing layer, whose thickness is 2B, but whose velocity is half that of the blood, and—notwithstanding the operational differences—behaves according to the Boltzmann result. Thus a 100 µm blood layer is treated as two 50 µM layers, each communicating with a 50 µm layer of sheathing fluid that is traveling with the same velocity as the blood. Urea extraction is 90% of its maximum value for equal flows when E equals 0.45. This corresponds to a value $Dt/B^2$ of 0.848 and requires, for molecules whose diffusion coefficients are in the neighborhood of $10^{-5}$ cm$^2$/sec a blood residence time in the contact area of 2.1 sec. The approximation has been validated with more precise finite-element calculations and is accurate within 5%.

How quickly will two streams, contacted in this manner, come to equilibrium? Boltzmann's result is a complex formula but can be represented graphically as in FIG. 11. For small molecules, with diffusion coefficients, D, equal to about $10^{-5}$ cm$^2$/sec, such as ions, sugars, and urea in blood, 90% equilibration will occur in about 2.1 sec, a remarkably short time that reflects the thinness of the layers and the absence of a membrane. For larger molecules, e.g. albumin (D equal to ~$5 \cdot 10^{-7}$ cm$^2$/sec) 95% equilibration will occur in about 42 sec. This difference might seem large enough to afford discrimination between small molecules and proteins, but it is not. (For the same exposure time, which is the condition to be met in any one device and flow, the best selectivity between small and large molecules depends on the square root of their diffusion coefficients, 1/4.5 for the case considered here. In most practical situations, the selectivity is, in fact, worse. In a simple, direct contact blood treatment, the plasma albumin pool would be completely removed long before there was reasonable depletion of urea in body water [13].) A membraneless interface, by itself, is indiscriminate.

A Recirculating Sheath

If the blood-contacting fluid is not dialyzing fluid but rather a continuously circulating fluid that is dialyzed in a small, conventional dialyzer, one has the system shown in FIG. 12. The governing principle of this system is that both the blood and the sheath fluid must transport what the conventional dialyzer permits them to transport—no more, no less. Any solute not removed by the conventional dialyzer accumulates in the sheath fluid and returns to the blood contactor. The same principle applies if the device that extracts material from the sheath fluid is a hemodiafilter, absorber, or chemical reactor.

The extraction device also controls volume transport, although the resultant situation in the blood contactor is a little harder to interpret. After a short startup period, the protein concentration in the sheath fluid exiting the blood-sheath contactor will come close to the protein concentration in blood. If water is ultrafiltered from the conventional dialyzer, the sheath fluid leaving the conventional dialyzer and returning to the blood-sheath fluid contactor will have a higher protein concentration that that in blood, and will thus be hyperosmotic. Water then passes from blood into the sheath fluid osmotically, without a hydrostatic pressure difference, at a rate set precisely by the ultrafiltration rate of the conventional dialyzer. How water is removed from the device that extracts materials from the sheath fluid is immaterial; only the amount removed is consequential. Thus, in this system, control of transport in the conventional dialyzer defines precisely both volume and solute transport out of the blood layer. One may, however, well ask, if there is a conventional dialyzer in the system, what overall advantage has been gained? There are at least three advantages: (1) Whole blood does not contact an artificial membrane; the blood interface is a pair of moving liquids. The interface should be highly biocompatible and cannot be fouled; anything that might deposit at the interface would be swept away. Because volume transport is osmotic, there is no tendency to draw cells to the interface. (2) Transport is very rapid. While one might ask whether transport in the conventional dialyzer is not now the limiting factor, the absence of cells in this device allows for higher rates of shear and ultrafiltration than would be possible if whole blood were present. (3) The shear stresses imparted to the blood layer are extremely low. The highest shear stress in the system is low and occurs in the sheath fluid where it contacts the wall.

Preventing Cells from Entering the Sheath Fluid

The systems presented here are effective if blood cells, particularly erythrocytes whose conservation is a recognized criterion of good dialysis, do not migrate into the sheath fluid. It is important to understand how stringent this requirement must be, although some ways of relaxing it will be discussed below. If 100 L of patient blood are dialyzed per week, and cell loss is kept at 1:10,000, the volumetric blood loss per week would be 10 ml, probably less than losses encountered in current therapies, and probably acceptable. Cells entering the sheath fluid must either remain there or return to the bloodstream, which they are unlikely to do, unaided. In certain embodiments of the system of the invention, there is no place for the small number of cells that may migrate into the sheath fluid to escape. FIG. 12 shows a flush port that allows for the intermittent injection of a small volume of sterile saline into the sheath fluid. Such an injection would force return of entrapped cells to the circulation. Because sheath fluid volume is less than 5 ml, displacing the entire sheath fluid volume into the bloodstream is equivalent to the volume removed in about 2 min of ultrafiltration.

The general tendency for cells to migrate to the center of a flowing stream is well documented [14-16]. In addition to this general phenomenon, it has been shown that when shear rates are low enough to allow rouleaux formation, the migration is even more pronounced [17]. Measurements of cell migration in a prototype membraneless device confirm that cells migrate well to the center of a smooth, steadily operated flow channel [13].

How Would A Real Ambulatory Dialyzer Perform?

An ambulatory dialyzer, through which blood is flowing at all times, need not be dialyzing at all times. In one embodiment of the invention, such a device might have a continuous blood flow of 40 ml/min and be attached to a source of dialysate 50% of the time, 84 hr/wk. Thus, just over 200 L of patient blood would be dialyzed per week. Because the flows in this device are concurrent and, in present designs, approximately equal, the maximum urea clearance will be relatively low, approximately 18 ml/min, leading to an estimated Kt/V of about 1.8. In one aspect, one can assume that volume transport might reach 15 L/wk, which could be accomplished during dialysis (3 ml/min) or continuously (1.5 ml/min), since dialysate is not required to produce ultrafiltrate through the conventional dialyzer unit. The rapid equilibration times for small molecules cited above lead to en-face contact areas between blood and sheath fluid of only about 50 $cm^{2[13]}$. (The actual contact area, because the sheath fluid contacts both sides of the bloodstream, is about 100 $cm^2$.) The change in pressure from entrance to exit of the blood-sheath contactor is about 5 mmHg.

Figure 13:
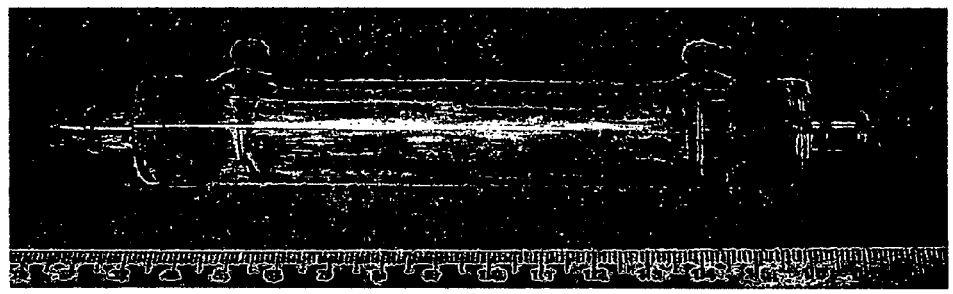
FIG. 13 is a photograph of a prototype of a miniaturized dialyzer. Fiber length is about 9 cm, with total surface area in the unit shown of 500 cm$^2$ of polysulfone hollow fiber. (Manufacturer: Saxonia Biotec, Radeberg, Germany.)

It is important to recall that blood flow is continuous in this system and that the starting and stopping of actual dialysis requires only the not-necessarily-sterile attachment and detachment, respectively, of dialysate leads. A patient is given a dialysis prescription in the form of the required number of hours per week of dialysis, and is left largely free to decide when to be attached to, or detached from, a source of dialysate. Most patients would accomplish the bulk of their dialysis overnight. The conventional dialyzer will foul, although more slowly because it operates in a cell-free, high-shear environment. It is possible that it will need to be replaced every other day. The invention provides for prototypes of this dialyzer, with areas of 500 and 1000 $cm^2$, for diffusive and hydraulic permeability and for the rate at which performance decrements. The shell for these devices looks like a mini-conventional dialyzer (FIG. 13).

What Would A Real Ambulatory Dialyzer Look Like?

Figure 14:
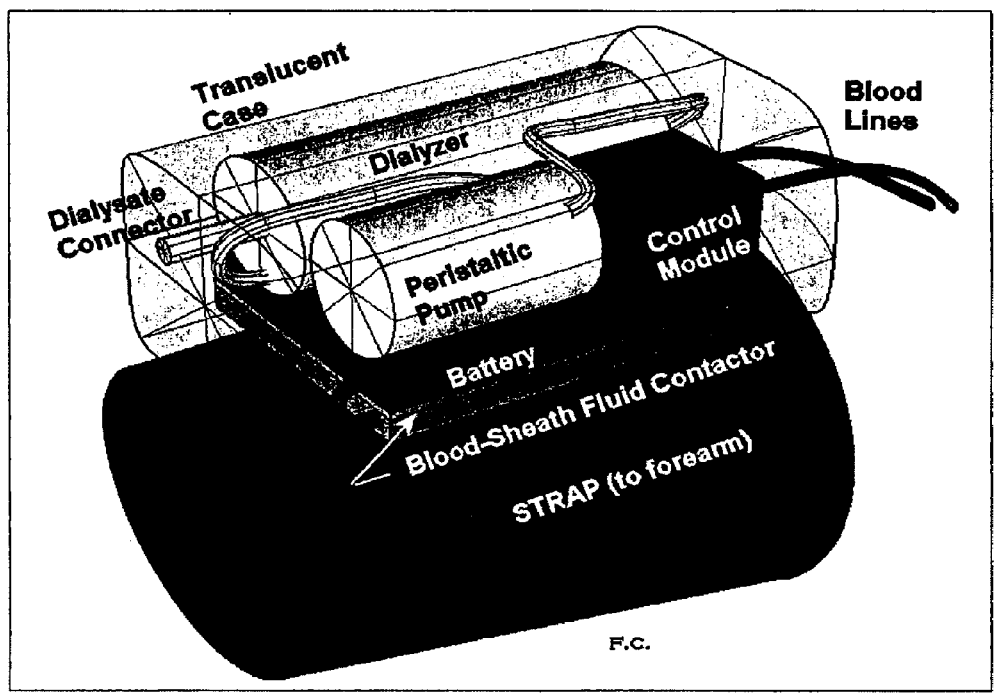
FIG. 14 is a schematic drawing of a wrist-size wearable dialysis system. The blood-sheath fluid contactor, shaped as a plate about 5.5×8 cm is sized to lie on the forearm. A two-headed peristaltic pump, dialyzer, and control module are mounted above the plate. Power for the pump can be provided by a battery shaped to match the dimensions of the contactor. The assembly would be placed under a smooth cover in actual patient use.

In one embodiment of the invention, the ambulatory dialyzer would be worn on the lower arm. The unit is comprised of five elements: (i) a blood-sheath contactor, a two-layer plate whose dimensions are about 5.5×8×0.6 cm; (ii) a conventional dialyzer of FIG. 13 reconfigured to have an elliptical or rectangular cross-section; (iii) a small, battery-operated, two-tube peristaltic pump that maintains both blood and sheath fluid flows; (iv) an exchangeable, rechargeable battery with dimensions similar to that of the blood sheath contactor; (v) a small control module. These elements are shown in one embodiment as they might be worn on a patient's forearm in FIG. 14. One approach is the use of two catheters similar to those that are used in long-term total parenteral nutrition.

An important concomitant of the proposed system is the ability of the patient to secure maintenance of his device by going to a service center. Some patients may be able to change the dialyzer module; others may wish assistance. Assistance could be provided at a walk-in service unit. With or without assistance, the proposed system is designed to empower patients in the management of their disease.

Other Realizations of the Membraneless Device

Plasmapheresis: The flowpath of the blood-sheath contactor appears to afford an excellent geometry for achieving plasmapheresis. Under these circumstances, an initial charge of sheath fluid would rapidly become equivalent to plasma and, during apheresis, a fraction of the circulating sheath fluid, equivalent to plasma, would be continuously withdrawn. Present plasmapheresis devices require either membrane contact or the application of centrifugal force. In this application of the membraneless flowpath, neither would be required.

Studies of molecular transport in blood: Membraneless transport offers a potentially important, non-clinical opportunity. The movement of many molecules through blood and, sometimes, through dialysate is poorly understood. This is true of molecules distributed across extracellular and intracellular space if their performance is not trivialized because they are either instantly equilibrated or completely unaffected as transport occurs. It is also true for molecules that are bound to slower-moving molecules or cell surfaces and dissociate from these havens as transport occurs. Finally it is true of molecules that change their molecular shape, or charge, or degree of aggregation with concentration. The transport of these molecules in blood is not fully understood, in large part because the study of this transport often occurs in the presence of a membrane whose dominant resistance obscures anomolous intraphase transport. For example, the factors limiting transport of phosphate, bilirubin and fatty acids in blood are not fully understood. Membraneless transport emphasizes exchange within phases, not across their boundary, and can even be conducted between contiguous layers of blood, only one of which, initially, contains the solute of interest.

Transport without molecular discrimination is valueless. Membraneless dialysis is, in fact, not possible, but membraneless transport coupled with sheath dialysis is possible and probably practical. It represents an advance over current membrane systems, especially in the much desired, but difficult to achieve, modality of long, slow, safe ambulatory renal replacement therapy.

REFERENCES

1. Blackshear, P. L., 2 New Concepts That Might Lead To A Wearable Artificial-Kidney. Kidney International, 1978: p. S133-S137.
2. Blaney, T. L., O. Lindan, and R. E. Sparks, Adsorption—A Step Toward A Wearable Artificial Kidney. Transactions American Society for Artificial Internal Organs, 1966. 12(APR): p. 7
3. Henne, W., et al., Wearable Artificial-Kidney. Artificial Organs, 1977. 1(1): p. 126-126.
4. Kolff, W. J., et al., Towards A Wearable Artificial-Kidney. Kidney International, 1976. 10: p. S300-S304.
5. Saito, A., et al., Maintaining Low Concentrations Of Plasma Beta(2)-Microglobulin Through Continuous Slow Hemofiltration. Nephrology Dialysis Transplantation, 1995. 10: p. 52-56.
6. Seo, S., et al., Improvement Of The Wearable Artificial-Kidney. Artificial Organs, 1981. 5(3): p. 321-321.
7. Vanholder, R. and S. Ringoir, Pitfalls Of Wearable Artificial-Kidney. International Journal Of Artificial Organs, 1990. 13(11): p. 715-719.
8. Giddings, J. C., Continuous Separation In Split-Flow Thin (Splitt) Cells—Potential Applications To Biological-Materials. Separation Science And Technology, 1988. 23(8-9): p. 931-943.
9. Levin, S. and G. Tawil, Analytical Splitt Fractionation In The Diffusion Mode Operating As A Dialysis-Like System Devoid Of Membrane—Application To Drug-Carrying Liposomes. Analytical Chemistry, 1993. 65(17): p. 2254-2261.

10. Fazio, F., Artificial Kidney and Methods of Using Same, in European Patent Register. 2002, Renal Plant Corp.: EU.
11. Ronco, C. Microfluidic, Membrane-Free Dialysis. in American Society of Nephrology, Annual Meeting. 2002.
12. Wellman, P. S., Substantially Inertia Free Hemodialysis. 2004: US.
13. Leonard, E. F., et al., Dialysis without membranes: How and why? Blood Purification, 2004. 22(1): p. 92-100.
14. Moger, J., et al., Measuring red blood cell flow dynamics in a glass capillary using Doppler optical coherence tomography and Doppler amplitude optical coherence tomography. Journal Of Biomedical Optics, 2004. 9(5): p. 982-994.
15. Singh, M. and A. T. V. Ramesh, Hematocrit Dependence Of Cellular Axial Migration And Tubular Pinch Effects In Blood-Flow Through Glass-Capillaries. Current Science, 1990. 59(4): p. 223-226.
16. Uijttewaal, W. S. J., E. J. Nijhof, and R. M. Heethaar, Lateral Migration Of Blood-Cells And Microspheres In 2-Dimensional Poiseuille Flow—A Laser-Doppler Study. Journal Of Biomechanics, 1994. 27(1): p. 35-42.
17. Goldsmith, H. L. and S. Spain, Margination Of Leukocytes In Blood-Flow Through Small Tubes. Microvascular Research, 1984. 27(2): p. 204-222.
18. Loschmidt J: Experimental—Untersuchungen uber die Diffusion von Gasen ohne porose Scheidewande. Sitzungsber Kais Akad Wiss Wien Math Naturwiss K1 II 1870; 61.367.
19. Wakeham W A, Kestin J: The measurement of diffusion coefficients, in Ho CY (ed): Transport Properties of Fluids. New York, Hemisphere, 1988, pp 225-228.

Persons skilled in the art will also appreciate that the present invention can be practiced by other than the described embodiments, which are presented for purposes of illustration and not of limitation, and that the present invention is limited only by the claims that follow.

What is claimed is:

1. A method of performing a blood treatment on a patient, the method comprising:
   attaching blood lines of a blood tubing set to a microfluidic channel;
   attaching a membrane-based filter device to the microfluidic channel so as to define a recirculating flowpath uninterrupted by a membrane;
   at a treatment time:
      attaching a source of dialysate to the membrane-based filter device such that the dialysate flows on one side of a membrane of the filter device;
      permitting toxins and water to pass from the microfluidic channel through the membrane of the filter device into the dialysate flow; and
      returning components of the patient's blood passing in the recirculating flowpath back to the patient's blood; and
   after the treatment time, disconnecting the source of dialysate while leaving the blood lines attached to the microfluidic channel.

2. The method of claim 1, further comprising, at a second treatment time after the disconnecting, repeating the attaching a source of dialysate, the permitting, and the returning.

3. The method of claim 2, further comprising, after the disconnecting and before the repeating, flowing blood and fluid together in the microfluidic channel.

4. The method of claim 1, wherein said permitting includes simultaneously flowing blood from the patient and fluid from the membrane-based filter device together in the microfluidic channel.

5. The method of claim 4, wherein the simultaneously flowing is such that the toxins and water move from the blood flow into the fluid from the membrane-based filter device without passing through any membrane.

6. The method of claim 1, wherein said components of the patient's blood include blood proteins.

7. A method of performing a blood treatment on a patient, the method comprising:
   co-flowing blood from the patient and recirculating fluid from a membrane-based filter device through a microfluidic channel such that toxins, water, and blood components are transferred from the blood flow into the recirculating fluid flow without passing through a membrane, the recirculating fluid flow with the toxins, water, and blood components exiting the microfluidic channel at an outlet thereof and returning to the membrane-based filter device;
   at a treatment time:
      connecting the membrane-based filter device to a source of dialysate; and
      flowing the dialysate from the source along a side of a membrane in the membrane-based filter device such that toxins and water in the recirculating fluid flow move across the membrane into the dialysate flow; and
   after the treatment time, disconnecting the membrane-based filter device from the source of dialysate.

8. The method of claim 7, wherein the co-flowing blood and recirculating fluid and the flowing the dialysate occur at a same time.

9. The method of claim 7, further comprising, after the disconnecting:
   continuing to co-flow the blood and the recirculating fluid through the microfluidic channel.

10. The method of claim 7, wherein the blood components in the recirculating fluid flow exiting the microfluidic channel are returned to the microfluidic channel.

11. The method of claim 10, wherein the co-flowing blood and recirculating fluid is such that the blood components in the exiting recirculating fluid flow are returned to the flowing blood.

12. The method of claim 7, wherein the blood components include albumin.

13. The method of claim 7, wherein the recirculating fluid exiting the microfluidic channel flows through the membrane-based filter device on an opposite side of the membrane and is returned to the microfluidic channel to co-flow with the blood therein.

14. A method of performing a blood treatment on a patient, the method comprising:
   flowing blood from the patient and recirculating fluid from a secondary processing device together along a microfluidic channel in a primary processing device such that toxins, water, and blood components are removed from the blood flow without passing through a membrane,
   conveying fluid with the removed toxins, water, and blood components therein from an outlet of the primary processing device to an upstream inlet of the primary processing device via a flowpath through the secondary processing device; and
   periodically using the secondary processing device to eliminate water and toxins from the fluid in the flowpath through the secondary processing device.

15. The method of claim 14, wherein the removed blood components at the outlet of the primary processing device are returned to the flowing blood in the microfluidic channel.

16. The method of claim 14, wherein:
the secondary processing device is a membrane-based filter device; and
water and toxins are eliminated from the fluid flowing through the filter device by passing the water and toxins across a membrane into a dialysate flow.

17. The method of claim 14, wherein the periodically using the secondary processing device includes:
connecting the secondary processing device to a source of dialysate; and
flowing the dialysate from the source along a side of a membrane in the secondary processing device such that the toxins and water move across the membrane into the dialysate flow while blood components are retained in the fluid flowing on an opposite side of the membrane.

18. The method of claim 14, wherein when the secondary processing device is not used to eliminate water and toxins, the secondary processing device is not connected to a source of dialysate.

* * * * *